(12) United States Patent
Dudley, Jr.

(10) Patent No.: US 9,114,133 B2
(45) Date of Patent: Aug. 25, 2015

(54) METHOD OF IMPROVING DIASTOLIC DYSFUNCTION

(71) Applicant: Samuel C. Dudley, Jr., Chicago, IL (US)

(72) Inventor: Samuel C. Dudley, Jr., Chicago, IL (US)

(73) Assignees: U.S. DEPT. OF VETERANS AFFAIRS, Washington, DC (US); THE BOARD OF TRUSTEES OF THE UNIV. OF ILLINOIS, Urbana, IL (US)

( * ) Notice: Subject to any disclaimer, the term of this patent is extended or adjusted under 35 U.S.C. 154(b) by 0 days.

(21) Appl. No.: 13/658,943

(22) Filed: Oct. 24, 2012

(65) Prior Publication Data

US 2013/0065903 A1    Mar. 14, 2013

Related U.S. Application Data

(63) Continuation-in-part of application No. 11/895,883, filed on Aug. 27, 2007.

(60) Provisional application No. 60/840,368, filed on Aug. 25, 2006, provisional application No. 61/552,500, filed on Oct. 28, 2011.

(51) Int. Cl.

| A61K 31/50 | (2006.01) |
| A61K 31/40 | (2006.01) |
| A61K 38/44 | (2006.01) |
| A61K 31/519 | (2006.01) |

(52) U.S. Cl.
CPC .............. *A61K 31/40* (2013.01); *A61K 31/519* (2013.01); *A61K 38/44* (2013.01)

(58) Field of Classification Search
USPC ........................................................ 514/249
See application file for complete search history.

(56) References Cited

U.S. PATENT DOCUMENTS

| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,624,665 A | 11/1986 | Nuwayser |
| 4,655,767 A | 4/1987 | Woodard et al. |
| 4,687,481 A | 8/1987 | Nuwayser |
| 4,797,284 A | 1/1989 | Loper et al. |
| 4,810,499 A | 3/1989 | Nuwayser |
| 4,834,978 A | 5/1989 | Nuwayser |
| 4,877,618 A | 10/1989 | Reed, Jr. |
| 4,880,633 A | 11/1989 | Loper et al. |
| 4,917,895 A | 4/1990 | Lee et al. |
| 4,927,687 A | 5/1990 | Nuwayser |
| 4,956,171 A | 9/1990 | Chang |
| 5,035,894 A | 7/1991 | Lee et al. |
| 5,059,595 A | 10/1991 | Le Grazie |
| 5,073,543 A | 12/1991 | Marshall et al. |
| 5,091,186 A | 2/1992 | Miranda et al. |
| 5,120,548 A | 6/1992 | McClelland et al. |
| 5,163,899 A | 11/1992 | Sibalis |
| 5,232,702 A | 8/1993 | Pfister et al. |
| 5,234,690 A | 8/1993 | Chiang et al. |
| 5,273,755 A | 12/1993 | Venktrama et al. |
| 5,273,756 A | 12/1993 | Fallon et al. |
| 5,308,625 A | 5/1994 | Wong et al. |
| 5,354,556 A | 10/1994 | Sparks et al. |
| 5,356,632 A | 10/1994 | Gross et al. |
| 5,358,715 A | 10/1994 | Wong et al. |
| 5,372,579 A | 12/1994 | Sibalis |
| 5,421,816 A | 6/1995 | Lipkovker |
| 5,466,465 A | 11/1995 | Royds et al. |
| 5,494,680 A | 2/1996 | Peterson |
| 5,505,958 A | 4/1996 | Bello et al. |
| 5,554,381 A | 9/1996 | Roos et al. |
| 5,560,922 A | 10/1996 | Chien et al. |
| 5,585,111 A | 12/1996 | Peterson |
| 5,591,767 A | 1/1997 | Mohr et al. |
| 5,639,476 A | 6/1997 | Oshlack et al. |
| 5,656,285 A | 8/1997 | Sablotsky et al. |
| 5,667,798 A | 9/1997 | Royds et al. |
| 5,674,533 A | 10/1997 | Santus et al. |
| 5,698,217 A | 12/1997 | Wilking |
| 5,733,566 A | 3/1998 | Lewis |
| 5,741,511 A | 4/1998 | Lee et al. |
| 5,747,783 A | 5/1998 | Myung et al. |
| 5,770,219 A | 6/1998 | Chiang et al. |
| 5,814,599 A | 9/1998 | Mitragotri et al. |
| 5,817,332 A | 10/1998 | Urtti et al. |
| 5,833,647 A | 11/1998 | Edwards |
| 5,849,732 A | 12/1998 | Suzuki et al. |
| 5,879,322 A | 3/1999 | Lattin et al. |
| 5,906,830 A | 5/1999 | Farinas et al. |
| 6,132,420 A | 10/2000 | Dionne et al. |

(Continued)

FOREIGN PATENT DOCUMENTS

| WO | WO 2007050585 A2 * | 5/2007 |
| WO | WO 2011/056572 A1 | 5/2011 |

OTHER PUBLICATIONS

U.S. Appl. No. 14/083,841, filed Nov. 19, 2013.
Office Action dated Nov. 22, 2013, in U.S. Appl. No. 11/895,883, filed Aug. 27, 2007.
Marantz et al. "The relationship between left ventricular systolic function congestive heart failure diagnosed by clinical criteria", 1988; Circulation; 77(3): 607-612.
Owan, et al., Trends in Prevalence and Outcome of Heart Failure with Preserved Ejection Fraction; The New England Journal of Medicine; Jul. 20, 2006; 355;3 pp. 251-259.
Davis ME, Cai H, McCann L, Fukai T, Harrison DG. Role of c-Src in regulation of endothelial nitric oxide synthase expression during exercise training. Am J Physiol Heart Circ Physiol; 284:H1449-1453, 2003 (First published Dec. 5, 2002).
Heymes C, Bendall JK, Ratajczak P, Cave AC, Samuel JL, Hasenfuss G, Shah AM. Increased myocardial NADPH oxidase activity in human heart failure. J Am Coll Cardiol. Jun. 18, 2003; 41(12):2164-71.

(Continued)

*Primary Examiner* — Shirley V Gembeh
(74) *Attorney, Agent, or Firm* — Dinesh Agarwal, P.C.

(57) ABSTRACT

A method of treating, preventing, reversing, or ameliorating diastolic dysfunction includes reducing S-glutathionylated myosin binding protein-C (MyBP-C) level by administering to a host in need thereof a therapeutically effective amount of tetrahydrobiopterin ($BH_4$).

10 Claims, 17 Drawing Sheets

(56) References Cited

U.S. PATENT DOCUMENTS

| | | | |
|---|---|---|---|
| 6,245,357 | B1 | 6/2001 | Edgren et al. |
| 6,270,787 | B1 | 8/2001 | Ayer |
| 6,283,953 | B1 | 9/2001 | Ayer et al. |
| 6,287,295 | B1 | 9/2001 | Chen et al. |
| 6,333,050 | B2 | 12/2001 | Wong et al. |
| 6,342,249 | B1 | 1/2002 | Wong et al. |
| 6,365,185 | B1 | 4/2002 | Ritschel et al. |
| 6,368,626 | B1 | 4/2002 | Bhatt et al. |
| 6,375,978 | B1 | 4/2002 | Kleiner et al. |
| 8,003,324 | B2 | 8/2011 | Dudley, Jr. |
| 2004/0091477 | A1 | 5/2004 | Haines et al. |
| 2006/0281668 | A1 | 12/2006 | Parobok et al. |
| 2012/0208762 | A1 | 8/2012 | Dudley |

OTHER PUBLICATIONS

Silberman et al. Uncoupled Cardiac Nitric Oxide Mediates Diastolic Dysfunction. Circulation. 2010;121:519-528; originally published online Jan. 18, 2010. With Supplemental Data (21 pages).

Yancy et al. 2013 ACCF/AHA Guideline for the Management of Heart Failure. Journal of the American College of Cardiology. vol. 62, No. 16, Oct. 15, 2013:e147-239.

Jeong, E.M. and Dudley, Jr. New Diagnostic and Therapeutic Possibilities for Diastolic Heart Failure. Rhode Island Medical Journal. Feb. 2014 vol. 97, No. 2, pp. 35-37.

Schocken DD, Benjamin EJ, Fonarow GC, Krumholz HM, Levy D, Mensah GA et al. Prevention of heart failure: a scientific statement from the American Heart Association Councils on Epidemiology and Prevention, Clinical Cardiology, Cardiovascular Nursing, and High Blood Pressure Research; Quality of Care and Outcomes Research Interdisciplinary Working Group; and Functional Genomics and Translational Biology Interdisciplinary Working Group. Circulation 2008;117:2544-65.

Owan TE, Hodge DO, Herges RM, Jacobsen SJ, Roger VL, Redfield MM. Trends in prevalence and outcome of heart failure with preserved ejection fraction. N Engl J Med 2006;355:251-9.

Ouzounian M, Lee DS, Liu PP. Diastolic heart failure: mechanisms and controversies. Nat Clin Pract Cardiovasc Med 2008;5:375-86.

Ziolo MT, Kohr MJ, Wang H. Nitric oxide signaling and the regulation of myocardial function. J Mol Cell Cardiol 2008;45:625-32.

Li et al. Aging induces cardiac diastolic dysfunction, oxidative stress, accumulation of advanced glycation endproducts and protein modification. Aging Cell. 4(2):57-64, Apr. 2005.

Landmesser U, Dikalov S, Price SR, McCann L, Fukai T, Holland SM et al. Oxidation of tetrahydrobiopterin leads to uncoupling of endothelial cell nitric oxide synthase in hypertension. J Clin Invest 2003;111:1201-9.

Flesch M, Kilter H, Cremers B, Lenz O, Sudkamp M, Kuhn-Regnier F et al. Acute effects of nitric oxide and cyclic GMP on human myocardial contractility. J Pharmacol Exp Ther 1997;281:1340-9.

Prabhu SD, Azimi A, Frosto T. Nitric oxide effects on myocardial function and force-interval relations: regulation of twitch duration. J Mol Cell Cardiol 1999;31:2077-85.

Ruetten H, Dimmeler S, Gehring D, Ihling C, Zeiher AM. Concentric left ventricular remodeling in endothelial nitric oxide synthase knockout mice by chronic pressure overload. Cardiovasc Res 2005;66:444-53.

Ungureanu-Longrois D, Bezie Y, Perret C, Laurent S. Effects of exogenous and endogenous nitric oxide on the contractile function of cultured chick embryo ventricular myocytes. J Mol Cell Cardiol 1997;29:677-87.

Silberman GA, Fan TH, Liu H, Jiao Z, Xiao HD, Lovelock JD et al. Uncoupled cardiac nitric oxide synthase mediates diastolic dysfunction. Circulation 2010;121:519-28, with Supplemental data (21 pages).

Vasquez-Vivar J, Kalyanaraman B. Generation of superoxide from nitric oxide synthase. FEBS Lett 2000;481:305-6.

Lovelock JD, Monasky MM, Jeong EM, Lardin HA, Liu H, Patel BG et al. Ranolazine improves cardiac diastolic dysfunction through modulation of myofilament calcium sensitivity. Circ Res 2012;110:841-50, with Supplemental Material (32 pages).

Adachi T, Weisbrod RM, Pimentel DR, Ying J, Sharov VS, Schoneich C et al. S-Glutathiolation by peroxynitrite activates SERCA during arterial relaxation by nitric oxide. Nat Med 2004;10:1200-7.

Adachi T, Pimentel DR, Heibeck T, Hou X, Lee YJ, Jiang B et al. S-glutathiolation of Ras mediates redox-sensitive signaling by angiotensin II in vascular smooth muscle cells. J Biol Chem 2004;279:29857-62, with Supplemental data (4 pages).

Chen FC, Ogut O. Decline of contractility during ischemia-reperfusion injury: actin glutathionylation and its effect on allosteric interaction with tropomyosin. Am J Physiol Cell Physiol 2006:290:C719-C727.

Kagawa K, Horiuti K, Yamada K. BDM compared with $P_i$ and low $Ca^{2+}$ in the cross-bridge reaction initiated by flash photolysis of caged ATP. Biophys J 1995;69:2590-600.

Wolska BM, Keller RS, Evans CC, Palmiter KA, Phillips RM, Muthuchamy M et al. Correlation between myofilament response to $Ca^{2+}$ and altered dynamics of contraction and relaxation in transgenic cardiac cells that express beta-tropomyosin. Circ Res 1999;84:745-51.

de Tombe PP, Stienen GJ. Protein kinase A does not alter economy of force maintenance in skinned rat cardiac trabeculae. Circ Res 1995;76:734-41 (26 pgs.).

de Tombe PP, ter Keurs HE. Force and velocity of sarcomere shortening in trabeculae from rat heart. Effects of temperature. Circ Res 1990;66:1239-54.

Martin AF, Phillips RM, Kumar A, Crawford K, Abbas Z, Lessard JL et al. $Ca^{2+}$ activation and tension cost in myofilaments from mouse hearts ectopically expressing enteric gamma-actin. Am J Physiol Heart Circ Physiol 2002;283:H642-H649.

Layland J, Cave AC, Warren C, Grieve DJ, Sparks E, Kentish JC et al. Protection against endotoxemia-induced contractile dysfunction in mice with cardiac-specific expression of slow skeletal troponin I. FASEB J 2005; 19:1137-9 (26 pgs).

Hill BG, Ramana KV, Cai J, Bhatnagar A, Srivastava SK. Measurement and identification of S-glutathiolated proteins. Methods Enzymol 2010;473:179-97.

Biesiadecki BJ, Kobayashi T, Walker JS, John SR, de Tombe PP. The troponin C G159D mutation blunts myofilament desensitization induced by troponin I Ser23/24 phosphorylation. Circ Res 2007;100:1486-93.

Tong CW, Stelzer JE, Greaser ML, Powers PA, Moss RL. Acceleration of crossbridge kinetics by protein kinase A phosphorylation of cardiac myosin binding protein C modulates cardiac function. Circ Res 2008;103:974-82, with Supplemental data (26 pgs).

Fraysse B, Weinberger F, Bardswell SC, Cuello F, Vignier N, Geertz B et al. Increased myofilament $Ca^{2+}$ sensitivity and diastolic dysfunction as early consequences of Mybpc3 mutation in heterozygous knock-in mice. J Mol Cell Cardiol 2012;52:1299-307.

Barefield D, Sadayappan S. Phosphorylation and function of cardiac myosin binding protein-C in health and disease. J Mol Cell Cardiol 2010;48:866-75.

El-Armouche A, Pohlmann L, Schlossarek S, Starbatty J, Yeh YH, Nattel S et al. Decreased phosphorylation levels of cardiac myosin-binding protein-C in human and experimental heart failure. J Mol Cell Cardiol 2007;43:223-9.

Decker RS, Decker ML, Kulikovskaya I, Nakamura S, Lee DC, Harris K et al. Myosin-binding protein C phosphorylation, myofibril structure, and contractile function during low-flow ischemia. Circulation 2005;111:906-12.

Yuan C, Guo Y, Ravi R, Przyklenk K, Shilkofski N, Diez R et al. Myosin binding protein C is differentially phosphorylated upon myocardial stunning in canine and rat hearts—evidence for novel phosphorylation sites. Proteomics 2006;6:4176-86.

Sadayappan S, Osinska H, Klevitsky R, Lorenz JN, Sargent M, Molkentin JD et al. Cardiac myosin binding protein C phosphorylation is cardioprotective. Proc Natl Acad Sci U S A 2006;103:16918-23, with Supplement (2 pgs).

Sadayappan S, Gulick J, Osinska H, Martin LA, Hahn HS, Dorn GW et al. Cardiac myosin-binding protein-C phosphorylation and cardiac function. Circ Res 2005;97:1156-63, with Online Supplement (17 pgs).

Stelzer JE, Patel JR, Walker JW, Moss RL. Differential roles of cardiac myosin-binding protein C and cardiac troponin I in the

(56) References Cited

OTHER PUBLICATIONS myofibrillar force responses to protein kinase A phosphorylation. Circ Res 2007;101:503-11, with Online Supplement (17 pgs).
Fukuda N, Wu Y, Nair P, Granzier HL. Phosphorylation of titin modulates passive stiffness of cardiac muscle in a titin isoform-dependent manner. J Gen Physiol 2005; 125:257-71.
Yamasaki R, Wu Y, McNabb M, Greaser M, Labeit S, Granzier H. Protein kinase A phosphorylates titin's cardiac-specific N2B domain and reduces passive tension in rat cardiac myocytes. Circ Res 2002;90:1181-88, with Supplement (6 pgs).
Kruger M, Kotter S, Grutzner A, Lang P, Andresen C, Redfield MM et al. Protein kinase G modulates human myocardial passive stiffness by phosphorylation of the titin springs Circ Res 2009;104:87-94, with Supplement material (10 pgs).
Shah AM, Prendergast BD, Grocott-Mason R, Lewis MJ, Paulus WJ. The influence of endothelium-derived nitric oxide on myocardial contractile function Int J Cardiol 1995;50:225-31.
Layland J, Li JM, Shah AM. Role of cyclic GMP-dependent protein kinase in the contractile response to exogenous nitric oxide in rat cardiac myocytes. J Physiol 2002;540:457-67.
Shah AM, Spurgeon HA, Sollott SJ, Talo A, Lakatta EG. 8-bromo-cGMP reduces the myofilament response to Ca2+ in intact cardiac myocytes Circ Res 1994;74:970-8.
Colson BA, Locher MR, Bekyarova T, Patel JR, Fitzsimons DP, Irving TC et al. Differential roles of regulatory light chain and myosin binding protein-C phosphorylations in the modulation of cardiac force development. J Physiol 2010;588:981-93.
Harris SP, Lyons RG, Bezold KL. In the thick of it: HCM-causing mutations in myosin binding proteins of the thick filament. Circ Res 2011;108:751-64, with Supplemental Material (10 pgs).
Yates LD, Greaser ML. Quantitative determination of myosin and actin in rabbit skeletal muscle. J Mol Biol 1983;168:123-41.
Fritz JD, Swartz DR, Greaser ML. Factors affecting polyacrylamide gel electrophoresis and electroblotting of high-molecular-weight myofibrillar proteins. Anal Biochem 1989;180:205-10.
Vahebi S, Kobayashi T, Warren CM, de Tombe PP, Solaro RJ. Functional effects of rho-kinase-dependent phosphorylation of specific sites on cardiac troponin. Circ Res 2005;96:740-747.
Borgstahl et al. The Structure of Human Mitochondrial Manganese Superoxide Dimutase Reveals a Novel Tetrameric Interface of Two 4-Helix Bundles, Cell 71;107-118, 1992.
McCord & Fridovch. Superoxide Dimutase. Journal of Biol Chem. 244:6049-6055, 1969.
Liochev and Fridovich. The effects of superoxide dimutase on H2O2 formation. Free Radical Biol & Medicine 42 1465-1469, 2007.
Dikalove et al. Therapeutic Targeting of Mitochondrial Superoxide in Hypertension. Circ Res. Jul. 9, 2010;107(1):106-16, with Supplement (12 pgs).
Hogg, et al.; Heart Failure with Preserved Left Ventricular Systolic Function; Journal of the American College of Cardiology; vol. 43, No. 3, 2004; pp. 317-327.
Zile, Heart Failure with Preserved Ejection Fraction: Is This Diastolic Heart Failure?; Journal of the American College of Cardiology; vol. 41, No. 9, 2003; pp. 1519-1522.
Masoudi, et al.; Gender, Age, and Heart Failure with Preserved Left Ventricular Systolic Function; Journal of the American College of Cardiology; vol. 41, No. 2, 2003; pp. 217.
Smith, et al.; Outcomes in Heart Failure, Patients with Preserved Ejection Fraction; Journal of the American College of Cardiology; vol. 41, No. 9, 2003; pp. 1510-1518.
Cleland, et al.; The Perindopril in Elderly People with Chronic Heart Failure (PEP-CHF) Study; European Heart Journal (2006) 27, pp. 2338-2345.
Massie, et al.; Irbesartan in Patients with Heart Failure and Preserved Ejection Fraction; The New England Journal of Medicine; 359;23; Dec. 4, 2008; 2456-2467.
Ahmed, et al.; Effects of Digoxion on Morbidity and Mortality in Diastolic Heart Failure: . . . Circulation; Journal of the American Heart Assoc.; Aug. 1, 2006; pp. 397-403.
Davis; Heart Failure with Preserved and Reduce Left Ventricular Ejection Fraction in . . . Circulation; Journal of the American Heart Assoc.; Nov. 25, 2008; pp. 2259-2267.
Hunt, et al.; ACC/AHA 2005 Guidelines for the Diagnosis and Management of Heart Failure in Adults; JACC; vol. 53, No. 14,2009, pp. 1-90.
Zile, et al.; New Concepts in Diastolic Dysfunction and Diastolic Heart Failure; Part I . . . Circulation; Journal of the American Heart Assoc.; Mar. 26, 2002; pp. 1387-1393.
Zile, et al.; New Concepts in Diastolic Dysfunction and Diastolic Heart Failure; Part 11 . . . Circulation; Journal of the American Heart Assoc.; Mar. 26, 2002; pp. 1503-1508.
Zile, et al.; Left Ventricular End-Diastolic Volume is Normal in Patients With Heart Failure and a Normal Ejection Fraction; JACC; vol. 49, No. 9, 2007; pp. 982-985.
Zile, et al.; Diastolic Heart Failure; Definitions and Terminology; Progress in Cardiovascular Diseases; vol. 47, No. 5; Mar./Apr. 2005; pp. 307-313.
Veldhuisen, et al.; Beta-Blockade with Nebivolol in Eldery Heart Failure Patients with Impaired and Preserved . . . ; JACC; vol. 53, No. 23, 2009; 2150-2158.
Flather, et al.; Randomized Trial to Determine the Effect of Nebivolol on Mortality . . . ; European Heart Journal; vol. 26, No. 3; 2005; pp. 215-225.
Yusuf, et al.; Effects of Candesartan in Patients with Chronic Heart Failure and Preserved Left-Ventricular Ejection Fraction . . . ; The Lancet; vol. 362; Sep. 6, 2003; pp. 777-781.
Little et al., Therapy for Diastolic Heart Failure, Aug. 20, 2005; Progress in Cardiovascular Diseases; 47(6): 380-388.
Ouzounian et al. Diastolic heart failure: mechanisms and controversies. Nature Clinical Practice Cardiovascular Medicine. 5(7):375-386, Jul. 2008.
Reed et al. FASEB Journal. The senescence-accelerated mouse: a model for the investigation of age-related oxidative stress and diastolic dysfunction. 22:Meeting Abstract Supplement, Mar. 2008, 970. 39 (2 pages).
Westermann et al. Cardiac Inflammation Contributes to Changes in the Extracellular Matrix in Patients with Heart Failure and Normal Ejection Fraction. Circulation Heart Failure. 2011;4:44-52.
Satpathy et al. Diagnosis and management of diastolic dysfunction and heart failure. American Family Physician. 73(5):841-846. Mar. 1, 2006.
Kuwahara et al. Transforming Growth Factor-β Function Blocking Prevents Myocardial Fibrosis and Diastolic Dysfunction in Pressure-Overloaded Rats. Circulation; 106:130-135, 2002.
Leask, Andrew. TGF-β, cardiac fibroblasts, and the fibrotic response. Cardiovascular Research. 74:207-212, Jul. 21, 2006.
Reed et al. Diastolic Dysfuntion is Associated with Cardiac Fibrosis in the Senecence-Accelerated Mouse. Circulation 120(18), Supplement 2, S762-S763, Nov. 3, 2009 (1 page).
Blom et al. Gene regulation of connective tissue growth factor: new targets for antifibrotic therapy? Matrix Biology 21 (2002) 473-482.
Hunt et al., ACC/AHA 2005 Guidline Update for the Diagnosis and Management of Chronic Heart Failure in the Adult: A Report of the American College of Cardiology . . . , Circulation 2005; 112;e154-e235, with Correction (2 pages).
Redfield et al. Burden of Systolic and Diastolic Ventricular Dysfunction in the Community JAMA, Jan. 8, 2003, vol. 289, No. 2; 194-202 (2003).
Harper, N.J. (1962). Drug Latentiation in Jucker, ed. *Progress in Drug Research*, 4:221-294.
Morozowich et al. (1977). Application of Physical Organic Principles to Prodrug Design in E. B. Roche ed. *Design of Biopharmaceutical Properties through Prodrugs and Analogs*, APhA; Acad. Pharm. Sci. pp. 344-391.
Higuchi T. E. B. Roche, ed. (1977). Prodrug and Drug Delivery—An overview. *Bioreversible Carriers in Drug in Drug Design, Theory and Application*, APhA. 1-25 pages.
Pauletti et al. (1997). Improvement of oral peptide bioavailability: Peptidomimetics and Prodrug Strategies, *Adv. Drug. Delivery Rev.* 27:235-256.
Mizen et al. (1998). The Use of Esters as Prodrugs for Oral Delivery of β-Lactam antibiotics, *Pharm. Biotech.* 11,:345-365.

(56) References Cited

OTHER PUBLICATIONS

Wermuth et al. (1996). Designing Prodrugs and Bioprecursors I. Carrier Prodrugs, *Pract. Med. Chem.* 671-696.

M. Asgharnejad (2000). Improving Oral Drug Transport via Prodrugs, *Transport Processes in Pharmaceutical Systems*, Marcell Dekker, p. 185-218.

Balant et al. (1990) Prodrugs for the improvement of drug absorption via different routes of administration, *Eur. J. Drug Metab. Pharmacokinet.*, 15(2): 143-153.

Balimane and Sinko (1999). Involvement of multiple transporters in the oral absorption of nucleoside analogues, *Adv. Drug Delivery Rev.*, 39(1-3):183-209.

Browne (1997). Fosphenytoin (Cerebyx), *Clin. Neuropharmacol.* 20(1): 1-12.

Bundgaard (1979). Bioreversible derivatization of drugs—principle and applicability to improve the therapeutic effects of drugs, *Arch. Pharm. Chemi.* 86(1): 1-39.

Banerjee PK et al. Design of Prodrugs based on enzyme-substrate specificity. (H. Bundgaard, ed.) (1985) *Design of Prodrugs*, New York: Elsevier. 93-133 pgs.

Fleisher et al. (1996). Improved oral drug delivery: solubility limitations overcome by the use of prodrugs, *Adv. Drug Delivery Rev.* 19(2): 115-130.

Fleisher et al. (1985). Design of prodrugs for improved gastrointestinal absorption by intestinal enzyme targeting, *Methods Enzymol.* 112: 360-81.

Farquhar D, et al. (1983). Biologically Reversible Phosphate-Protective Groups, *J. Pharm. Sci.*, 72(3): 324-325.

Han, H.K. et al. (2000). Targeted prodrug design to optimize drug delivery, *AAPS PharmSci.*, 2(1): E6; 1-11 pages.

Sadzuka Y. (2000). Effective prodrug liposome and conversion to active metabolite, *Curr. Drug Metab.*, 1(1):31-48.

D.M. Lambert (2000) Rationale and applications of lipids as prodrug carriers, *Eur. J. Pharm. Sci.*, 11 Suppl 2:S15-27.

Wang, W. et al. (1999) Prodrug approaches to the improved delivery of peptide drugs. *Curr. Pharm. Des.*, 5(4):265-87.

Section 3 of the Dietary Supplement Health and Education Act of 1994, Public Law 103-417, Oct. 25, 1994, 8 pages.

Abdou, HM. Dissolution. Remington's Pharmaceutical Sciences, 18th ed., Mack Publishing, Easton, PA. (1990).

Allen TM et al. Drug Delivery Systems: Entering the Mainstream. Science.303 (5665):1818-22 (2004).

Jens T. Carstensen, Drug Stability: Principles & Practice, 379-80 (2nd ed., Marcel Dekker, NY, N.Y.: 1995.

Kim, Cherng-ju, Controlled Release Dosage Form Design, 2 (Technomic Publishing, Lancaster, Pa.: 2000), 3 pages.

Kim, Cherng-ju, Controlled Release Dosage Form Design, 231-238 (Technomic Publishing, Lancaster, Pa.: 2000, 7 pages.

Freireich EJ, et al., Quantitative Comparison of Toxicity of Anticancer Agents in Mouse, Rat, Hampster, Dog, Donkey, Monkey and Man. *Cancer Chemother Rep* 50:219-244, 1966.

Transdermal Drug Delivery Systems, Ointments, Creams, Lotions & Other Preparations. Transdermal Drug Delivery System 291-320 pgs. Introduction to Pharmaceutical Dosage Forms, 4th ed., Lea & Febiger, Philadelphia, Pa. (1985).

U.S. Appl. No. 12/929,786, filed Feb. 16, 2011.
U.S. Appl. No. 13/067,953, filed Jul. 11, 2011 (Abandoned).
U.S. Appl. No. 13/507,319, filed Jun. 21, 2012.
U.S. Appl. No. 13/551,790, filed Jul. 18, 2012.
U.S. Appl. No. 11/707,882, filed Feb. 20, 2007.
U.S. Appl. No. 13/091,972, filed Apr. 21, 2011.
U.S. Appl. No. 13/585,396, filed Aug. 14, 2012.
U.S. Appl. No. 11/895,883, filed Aug. 27, 2007.
Restriction Requirement dated Apr. 27, 2009, in U.S. Appl. No. 11/895,883, filed Aug. 27, 2007.
Office Action dated Aug. 3, 2009, in U.S. Appl. No. 11/895,883, filed Aug. 27, 2007.
Office Action (Final Rejection) dated Jan. 27, 2010, in U.S. Appl. No. 11/895,883, filed Aug. 27, 2007.

Verma et al. Novel cardioprotective effects of tetrahydrobiopterin after anoxia and reoxygenation: Identifying cellular targets for pharmacologic manipulation; 2002; The Journal of Thoracic and Cardiovascular Surgery; 123(6): 1074-1083.

Office Action dated Sep. 14, 2012, in U.S. Appl. No. 12/929,786, filed Feb. 16, 2011.
Office Action dated Oct. 12, 2012, in U.S. Appl. No. 13/091,972, filed Apr. 21, 2011.
Advisory Action dated Apr. 5, 2010, in U.S. Appl. No. 11/895,883, filed Aug. 27, 2007.

Achan V, Broadhead M, Malaki M, Whitley G, Leiper J, MacAllister R, Vallance P. Asymmetric dimethylarginine causes hypertension and cardiac dysfunction in humans and is actively metabolized by dimethylarginine dimethylaminohydrolase. Arterioscler Thromb Vasc Bioi 2003;23:1455-9.

Aisaka K, Gross SS, Griffith OW, Levi R. $N^G$-methylarginine, an inhibitor of endothelium-derived nitric oxide synthesis, is a potent pressor agent in the guinea pig: does nitric oxide regulate blood pressure in vivo? Biochem Biophys Res Commun 1989;160:881-6.

Amado LC, Saliaris AP, Raju SV, Lerkhe S, St. John M, Xie J, et aL Xanthine oxidase inhibition ameliorates cardiovascular dysfunction in dogs with pacing-induced heart failure. J Mol Cell Cardiol 39 (2005);531-536.

Antonozzi I, Carducci C, Vestri L, Pontecorvi A, Moretti F. Rapid and sensitive method for high-performance liquid chromatographic analysis of pterins in Biological fluids, J Chromatogr 1988;459:319-24.

Aurigemma G, Gaasch W. Diastolic Heart Failure. N Engl J Med 2004;351:1097-105.

Belvisi MG, Haddad EB, Battram C, Birrell M, Foster M, Webber S. Anti-inflammatory properties of ebselen in a model of sephadex-induced lung inflammation. Eur Respir J 2000;15:579-81.

Boger RH, Bode-Boger SM, Szuba A, Tsao PS, Chan JR, Tangphao 0, Blaschke TF, Cooke JP. Asymmetric dimethylarginine (ADMA): a novel risk factor for endothelial dysfunction: its role in hypercholesterolemia. Circulation 1998;98: 1842-7.

Boger RH. The emerging role of asymmetric dimethylarginine as a novel cardiovascular risk factor. Cardiovasc Res 2003;59:824-33.

Bosch-Morell F, Roma J, Puertas FJ, Marin N, Diaz-Llopis M, Romero FJ. Efficacy of the antioxidant ebselen in experimental uveitis. Free Radic Biol Med. 1999;27:388-91.

Boulden BM, Widder JD, Allen JC, Smith DA, Al-Baldawi RN, Harrison DG, Dikalov SI, Jo H, Dudley SC. Early determinants of$H_2O_2$-induced endothelial dysfunction. Free Radic Biol Med 41 (2006) 810-817.

Brun P, Tribouilloy C, Duval AM, 1serin L, Meguira A, Pelle G, et al. Left ventricular flow propagation during early filling is related to wall relaxation: a color M-mode Doppler analysis. J Am Coll Cardiol1992;20:420-32.

Brutsaert DL, Fransen P, Andries LJ, De Keulenaer GW, Sys S. U. Cardiac endothelium and myocardial function. Cardiovasc Res 1998;38:281-90.

Brutsaert DL. Cardiac endothelial-myocardial signaling: Its role in cardiac growth, contractile performance, and rhythmicity. Physiol Rev 2003;83:59-115.

Cai H, Li Z, Goette A, Mera F, Honeycutt C, Feterik K, Wilcox in, Dudley SC, Jr., Harrison DG, Langberg JJ. Downregulation of endocardial nitric oxide synthase expression and nitric oxide production in atrial fibrillation: potential mechanisms for atrial thrombosis and stroke. Circulation 2002; 106:2854-8.

Cai H, Li Z, Davis ME, Kanner W, Harrison DG, Dudley SC. Akt-dependent phosphorylation of serine 1179 and mitogen-activated protein kinase kinase/extracellular signal-regulated kinase 112 cooperatively mediate activation of the endothelial nitric-oxide synthase by hydrogen peroxide. Mol Pharmacol 2003;63:325-331.

Cingolani OH, Yang X-P, Cavasin MA, Carretero An. Increased systolic performance with diastolic dysfunction in adult spontaneously hypertensive rats. Hypertension 2003;41 :249-54.

Dikalov S, Fink B. ESR techniques for the detection of nitric oxide in vivo and in tissues. Methods Enzymol 2005;396:597-610.

Dudley SC, Hoch NE, McCann LA, Honeycutt C, Diamandopoulos L, Fukai T, Harrison DG, Dikalov SI, Langberg J. Atrial Fibrillation

(56) References Cited

OTHER PUBLICATIONS

Increases Production of Superoxide by the Left Atrium and Left Atrial Appendage: Role of the NADPH and Xanthine Oxidases. Circulation 2005;112,1266-73.

Duval-Moulin AM, Dupouy P, Brun P, Zhuang F, Pelle G, Perez Y, et el. Alteration of left ventricular diastolic function during coronary angioplasty-induced ischemia: a color M-mode Doppler study. J Am Coll Cardiol1997;29:1246-55.

Esterbauer H, Schaur RJ, Zollner H. Chemistry and biochemistry of 4-hydroxynonenal, malonaldehyde and related aldehydes. Free Radic Biol Med 1991;11:81-128.

Forstermann U, Munzel T. Endothelial nitric oxide synthase in vascular disease: from marvel to menace. Circulation 2006; 113: 1708-14.

Friedemann MN, Robinson SW, Gerhardt GA. o-Phenylenediamine-modified carbon fiber electrodes for the detection of nitric oxide. Anal Chern 1996;68:2621-8.

Garcia MJ, Ares MA, Asher C, Rodriguez L, Vandervoort P, Thomas ID. An index of early left ventricular filling that combined with pulsed Doppler peak E velocity may estimate capillary wedge pressure. J Am Coll Cardiol1997;29:448-54.

Garcia MJ, Palac RT, Malenka DJ, Terrell P, Plehn JF. Color M-mode Doppler flow propagation velocity is a relatively preload-independent index of left ventricular filling. J. Am Soc Echocardiogr 1999;12:129-37 (12 pages).

Garcia MJ, Smedira NG, Greenburg NL, Main M, Firstenberg MS, Odabashian J, et. al. Color M-mode Doppler flow propagation velocity is a preload insensitive index of 25 left ventricular relaxation: animal and human validation. J Am Coll Cardiol 2000;35:201-8.

Gladilin S, Bidmon HJ, Divanach A, Arteel GE, Witte OW, Zilles K, Sies H. Ebselen lowers plasma interleukin-6 levels and glial heme oxygenase-I expression after focal photothrombotic brain ischemia. Arch Biochem Biophys 2000;380:237-42.

Griendling KK, Sorescu D, Ushio-Fukai M. NAD(P)H oxidase: role in cardiovascular biology and disease. Cir Res 2000;86:494-501.

Gyurko R, kuhlencordt P, Fishman MC, Huang PL. Modulation of mouse cardiac function in vivo by eNOS and ANP. Am J Physiol Heart Circ Physiol 2000;278:H971-81.

Hart CM, Kleinhenz DJ, Dikelov sr, Boulden BM, Dudley sc. The measurement of nitric oxide production by cultured endothelial cells. Methods Enzymol 2005;396:502-14.

Hill MF, Singal PK. Right and left myocardial antioxidant responses during heart failure subsequent to myocardial infarction. Circulation 1997;96:2414-20 (15 pgs).

Hsieh E, Segal BH, Pagano PJ, et aL Vascular effects following homozygous disruption of $p^{47phox}$: an essential component of NADPH oxidase. Circulation 2000;101:1234-6.

Hunt SA, Abraham WT, Chin MR, Feldman AM, Francis GS, Ganiats TG, Jessup M, Konstam MA, Mancini DM, Michl K, Oates JA, Rahko PS, Silver MA, Stevenson LW, Yancy CWo ACC/AHA 2005 guideline update for the diagnosis and management of chronic heart failure in the adult: a report of the American College of Cardiology/American Heart Association Task Force on Practice Guidelines (Writing Committee to Update the 2001 Guidelines for the Evaluation and Management of 15 Heart Failure). American College of Cardiology Circ 2005; 112; e154-e235, with Correction (2 pages).

Ishii Y, Hashimoto K, Hirano K, Morishima Y, Mochizuki M, Masuyama K, Nomura A, Sakamoto T, Uchida Y, Sagai M, Sekizawa K. Ebselen decreases ozone-induced pulmonary inflammation in rats. Lung 2000;178:225-34.

Kadiiska MB, Burkitt MJ, Xiang QH, Mason RP. Iron supplementation generates hydroxyl radical in vivo: an ESR spin-trapping investigation. J Clin Invest 1995;96:1653-7.

Kawai K, Qin F, Shite J, Mao W, Fukuoka S, Liang CS. Importance of antioxidant and antiapoptotic effects of beta-receptor blockers in heart failure therapy. Am J Physiol Heart Circ Physiol 2004;287:HI003-12.

Kawashima S, Yokoyama M. Dysfunction of endothelial nitric oxide synthase and atherosclerosis. Arterioscler Thromb Vasc Bioi 2004;24:998-1005.

Kerr S, Brosnan MJ, McIntyre M, Reid JL, Dominiczak AF, Hamilton CA. Superoxide anion production is increased in a model of genetic hypertension. Role of the endothelium. Hypertension 1999;33:1353-8.

Kureishi Y, Luo Z, Shiojima I, et a!. The HMG-CoA reductase inhibitor simvastatin activates the protein kinase Akt and promotes angiogenesis in normocholesterolemic animals. Nat Med 2000;6:1004-10.

Kuzkaya N, Weissmann N, Harrison DG, Dikalov S. Interactions of peroxynitrite, tetrahydrobiopterin, ascorbic acid, and thiols: Implications for uncoupling endothelial nitric-oxide synthase. J Biol Chern 2003;278:22546-54.

Landmesser D, Cai H, Dikalov S, et al. Role of $p47^{phox}$ in vascular oxidative stress and hypertension caused by angiotensin II. Hypertension 2002;40:511-5.

Landmesser D, Dikalov S, Price SR, McCann L, Fukai T, Holland SM, Mitch WE, Harrison DG. Oxidation of tetrahydrobiopterin leads to uncoupling of endothelial cell nitric oxide synthase in hypertension. J Clin Invest 2003; 111: 1201-9.

Laude K, Cai H, Fink B, Hoch N, Weber DS, McCann L, Kojda G, Fukai T, Schmidt HR, Dikalov S, Ramasamy S, Gamez G, Griendling KK, Harrison DG. Hemodynamic and biochemical adaptations to vascular smooth muscle overexpression of $p22^{phox}$ in mice. Am. J Phvsiol Heart Circ Physiol2005;288:H7-12.

Laursen JB, Somers M, Kurz S, McCann L, Warnholtz A, Freeman BA, Tarpey M, Fukai T, Harrison DG. Endothelial regulation of vasomotion in ApoE-deficient mice: implications for interactions between peroxynitrite and tetrahydrobiopterin.Circulation 2001; 103: 1282-88.

Lavigne MC, Malech HL, Holland SM, et al. Genetic demonstration of p47phox-dependent superoxide anion production in murine vascular smooth muscle cells. Circulation 2001;104:79-84.

Lee SH, Oe T, Blair IA. Vitamin C-induced decomposition of lipid hydroperoxides to endogenous genotoxins. Science 2001;292:2083-6.

Li J-M, Mullen AM, Yun S, et al. Essential role of the NADPH oxidase subunit p47phox in endothelial cell superoxide production in response to phorbol ester and tumor necrosis factor-α. Circ Res 2002;90:143-50.

Lowry OH, Rosebrough NJ, Farr AL, Randall RJ. Protein measurement with the Folin phenol reagent. J Biol Chern 1951;193:265-75.

Lundin S, Friberg P, Ricksten SE. Diastolic properties of the hypertrophied left ventricle in spontaneously hypertensive rats. Acta Physiol Scand 1983; 118: 1-9 (5 pgs).

Mattioli AV, Zennaro M, Donatti S, Bonetti L, Mattioli G. Regression of Left ventricular hypertrophy and improvement of diastolic function in hypertensive patients treated with telmisartan. Int J Cardiol2004;97:383-388.

Meininger CJ, Marinos RS, Hatakeyama K, Martinez-Zaguilan R, Rojas JD, Kelly KA, Wu G. Impaired nitric oxide production in coronary endothelial cells of the spontaneously diabetic BB rat is due to tetrahydrobiopterin deficiency. Biochem J 2000;349:353-356.

Mital S, Zhang X, Zhao G, Bernstein RD, Smith CJ, Fulton DL, Sessa WC, Liao JK, Hintze TH. Simvastatin upregulates coronary vascular endothelial nitric oxide production in conscious dogs. Am J Physiol Heart Circ Physio 2000; 279: H2649-2657.

Nakamura R, Egashira K, Machida Y, Hayashidani S, Takeya M, Utsumi H, Tsutsui H, and Takeshita A. Probucol attenuates left ventricular dysfunction and remodeling in tachycardia-induced heart failure: roles of oxidative stress and inflammation. Circulation 2002; 106:362-367.

Nishihara K, Mikami T, Takatsuji H, et al. Usefulness of early diastolic flow propagation velocity measured by color M-mode Doppler technique for the assessment of left ventricular diastolic function in patients with hypertrophic cardiomyopathy. J Am Soc Echocardiogr 2000;13:801-8 (15 pgs).

Oudit GY, Sun H, Trivieri MG, et al. L-type Ca2+ channels provide a major pathway for iron entry into cardiomyocytes in iron-overload cardiomyopathy. Nat Med 2003;9:1187-94.

Oudit GY, Trivieri MG, Khaper N, Husain T, Wilson GJ, Liu P, Sole MJ, Backx PH. Taurine supplementation reduces oxidative stress and improves cardiovascular function in an iron-overload murine model. Circulation 2004;109:1877-85.

(56) References Cited

OTHER PUBLICATIONS

Pinsky DJ, Patton S, Mesaros S, Brovkovych V, Kubaszewski E, Grunfeld S, Malinski T. Mechanical transduction of nitric oxide synthesis in the beating heart. Circ Res 1997;81:372-9 (29 pgs).

Paulus WJ. Beneficial Effects of Nitric Oxide on Cardiac Diastolic Function: 'The Flip Side of the Coin'. Heart Failure Reviews 2000;5:337-44.

Qi X, Li K, Rouleau JL. Endocardial endothelium and myocardial performance in rats: effects of changing extracellular calcium and phenylephrine. J Mol Cell Cardiol 1996;28:859-69.

Qi XL, Stewart DJ, Gosselin H, Azad A, Picard P, Andries L, Sys SU, Brutsaert DL, Rouleau JL. Improvement of endocardial and vascular endothelial function on myocardial perfornlance by captopril treatment in postinfarct rat hemis. Circulation 1999;100: 1338-45.

Redfield MM, Jacobsen SJ, Burnett JC Jr, Mahoney DW, Bailey KR, Rodeheffer RJ. Burden of systolic and diastolic ventricular dysfunction in the community: appreciating the scope of the heart failure epidemic. JAMA 2003;289:194-202.

Sakata Y, Yamamoto K, Mano T, Nishikawa N, Yoshida J, Nakayama H, Otsu K, Suzuki K, Tada M, Hori M, Miwa T, Masuyama T. Angiotensin II type 1 receptor blockade prevents diastolic heart failure through modulation of Ca(2+) regulatory proteins and extracellular matrix. J Hypertens 2003; 21:1737-45.

Sarkar D, Vallance P, Harding SE. Nitric oxide: not just a negative inotrope. Eur J Heart Fail 2001;3:527-34.

Schaefer A, Klein G, Brand B, Lippolt P, Drexler H, Meyer GP. Evaluation of left ventricular diastolic function by pulsed Doppler tissue imaging in mice. J Am Soc Echocardiogr 2003;16:1144-9.

Schmidt AG, Gerst M, Zhai J, Carr AN, Pater L, Kranias EG, Hoit BD. Evaluation of left ventricular diastolic function from spectral and color M-mode Doppler in genetically altered mice. J Am Soc Echocardiogr 2002;15:1065-73.

Shah AM, Grocott-Mason RM, Pepper CB, Mebazaa A, Henderson AH, Lewis MJ, Paulus WJ. The cardiac endothelium: cardioactive mediators. Prog Cardiovasc Dis 1996;39:263-84.

Shinozaki K, Nishio Y, Okamura T, Yoshida Y, Maegawa H, Kojima H, Masada M, Toda N, Kikkawa R, Kashiwagi A. Oral administration of tetrahydrobiopterin prevents endothelial dysfunction and vascular oxidative stress in the aortas insulin resistant rats; Circ Res 200 (); 87: 566-73.

Singal PK, Khaper N, Farahmand F, and Bello-Klein A. Oxidative stress in congestive heart failure. Curr Cardiol Rep 2000;2:206-11.

Sohn D-W, Chai I-H, Lee D-J, Kim H-C, Kim H-S, Oh B-H, Lee M-M, Park Y -B, Choi Y-S, Seo J-D, Lee Y-W. Assessment of mitral annulus velocity by Doppler tissue imaging in the evaluation of left ventricular diastolic function. J Am Coll Cardiol 1997;30:474-80.

Stugaard M, Smiseth OA, Risoe C, Ihlen H. Intraventricular early diastolic filling during acute myocardial ischemia: assessment by multigated color M-mode Doppler echo cardiography. Circulation 1993;88:2705-13.

Stugaard M, Brodahl D, Torp H, Hen H. Abnormalities of left ventricular filling in patients with coronary artery disease: assessment by colour M-mode Doppler technique. Eur. Heart J 1994;15:318-27.

Sys SU, Pellegrino D, Mazza R, Gattuso A, Andries LJ, Tota L. Endocardial endothelium in the avascular heart of the frog: morphology and role of nitric oxide. J Exp Biol. 1997;200:3109-18.

Takatsuji H, Mikami T, Drasawa K, et al. A new approach for evaluation of left ventricular diastolic function: spatial and temporal analysis of left ventricular filling flow propagation By color M-mode Doppler echocardiography. J Am Coll Cardiol 1996;27:365-71.

Takimoto E, Champion HC, Li M, Ren S, Rodriguez Er, Tavazzi B, Lazzarino G, Paolocci N, Gabrielson KL, Wang Y, Kass DA. Oxidant stress from nitric oxide synthase-3 uncoupling stimulates cardiac pathologic remodeling from chronic pressure load. J Clin. Invest 2005:115:1221-31.

Thomas JD, Garcia MJ, Greengurg NL. Application of color Doppler M-mode echo cardiography in the assessment of ventricular diastolic function: potential for quantitative analysis. Heart Vessels 1997;Suppl12:135-7.

Ursell PC and Mayes M. The majority of nitric oxide synthase in pig heart is vascular and not neural. Cardiovasc Res 1993;27:1920-4.

Ursell PC and Mayes M. Anatomic distribution of nitric oxide synthase in the heart. Int J Cardiol 1995;50:217-23.

Vasquez-Vivar J, Kalyanaraman B, Martasek P, Hogg N, Masters BS, Karoui H, Tordo P, Pritchard KA Jr. Superoxide generation by endothelial nitric oxide synthase: the influence of cofactors. Proc Natl Acad Sci USA 1998;95:9220-25.

Vejlstrup NG, Bouloumie A, Boesgaard S, Andersen CB, Nielsen-Kudsk JE, Mortensen SA, Kent JD, Harrison DG, Busse R, Aldershvile J. Inducible nitric oxide synthase (iNOS) in the human heart: expression and localization in congestive heart failure. J Mol Cell Cardiol 1998;30:1215-23.

Wachtell K, Bella In, Rokkedal J, Palmieri V, Papademetriou V, DahlofB, Aalto T, Gerdts Devereux RB. Change in diastolic left ventricular filling after one year of antihypertensive treatment: The Losartan Intervention for Endpoint Reduction in Hypertension (LIFE) Study. Circulation 2002;105:1071-6.

Weiss JL, Frederiksen JW, Weisfeldt ML. Hemodynamic determinants of the time course of fall in canine left ventricular pressure. J Clin Invest 1976;58:751-60.

Xiao RD, Fuchs S, Campbell DJ, Lewis W, Dudley SC, Kasi VS, Hoit BD, Keshelava G, Zhao H, Campecchi MR, Bernstein KE. Mice with cardiac restricted angiotensin converting enzyme (ACE) have atrial enlargement, cardiac arrhythmia and sudden death. Am J Pathol 2004;165:1019-32.

Yang D, Levens N, Zhang IN, Vanhoutte PM, Feletou M. Specific potentiation of endothelium-dependent contractions in SHR by tetrahydrobiopterin. Hypertension 2003;41:136-42.

Zakynthinos E, Pierutsakos CH, Konstantinidis K, Zakynthinos S, Papadogiannis D. Losartan reduces left ventricular hypertrophy proportionally to blood pressure reduction in hypertensives, but does not affect diastolic cardiac function. Angiology 2004;55:669-78.

Zhang H, Schmeisser A, Garlichs CD, Plotze K, Damme D, Mugge A, Daniel WG. Angiotensin II-induced superoxide anion generation in human vascular endothelial cells: role of membrane-bound NADH-INADPH-oxidases. Cardiovasc Res 1999;44:215-22.

Zile MR, Brutsaert D. New Concepts in Diastolic Dysfunction and Diastolic Heart Failure: Part II. Circulation 2002;105:1503-8.

Zile MR, Baicu CF, Gaasch WH. Diastolic heart failure—Abnormalities in active relaxation and passive stiffness of the left ventricle. N Engl J Med 2004;350:1953-9.

Zou MH, Shi C, Cohen RA. 2002. Oxidation of the zinc-thiolate complex and uncoupling of endothelial nitric oxide synthase by peroxynitrite. J Clin Invest 2002;109:817-26.

Brutsaert et al. Relaxation and Disatole of the Heart. Physiological Reviews vol. 69, No. 4, 1228-1315,1989.

Nishida et al. Cell-Cell Signaling between Adult Rat Ventricular Mycocytes and Cardiac Microvascular Endothelial Cells in Hetertypic Primary Culture. J. Clin Invest 1993. 91:1934-1941.

Ramaciotti et al. Endothelial cells regulate cardiac contractility. Proc. Natl Acad. Sci. vol. 89. pp. 4033-4036, 1992.

Smith et al. Factors Released from Endocardiu of the Ferret and Pig Modulate Myocardial Contraction. Journal of Physiology (1991) 439, pp. 1-14.

Mugge A, Elwell JH, Peterson TE et al. Chronic treatment with polyethylene-glycolated superoxide dismutase partially restores endothelium-dependent vascular relaxations in cholesterol-fed rabbits. Circ Res 1991; 69:1293-300.

Kang JY, Chen Y and Epstein PN. Suppression of Doxorubicin Cardiotoxicity by Overexpression of Catalase in the Heart of Transgenic Mice. J. Bio Chem 1996; 271:12610-6.

Final Rejection dated Mar. 11, 2013, in U.S. Appl. No. 12/929,786, filed Feb. 16, 2011.

Office Action dated Apr. 2, 2013, in U.S. Appl. No. 11/707,882, filed Feb. 20, 2007.

Saito-Hisaminato A. et al. Genome-Wide Profiling of Gene Expressionin 29 Normal Human Tissues with a cDNA Microarray. DNA Research 9, 35-45 (2002).

* cited by examiner

Pulse-wave Doppler Images

Tissue Doppler Images

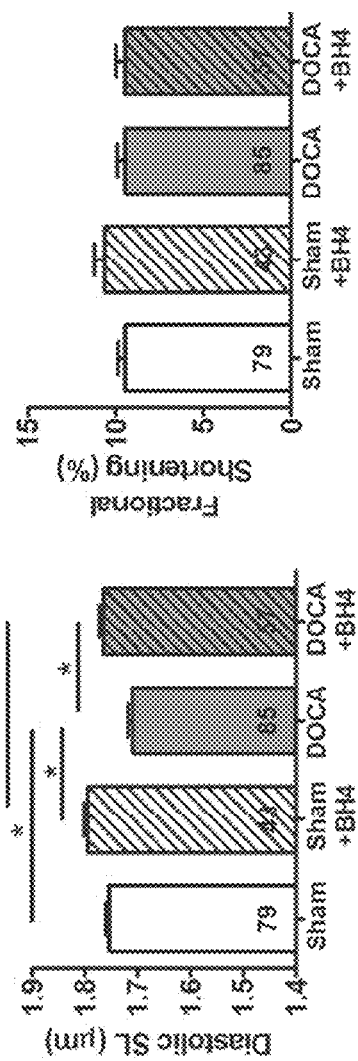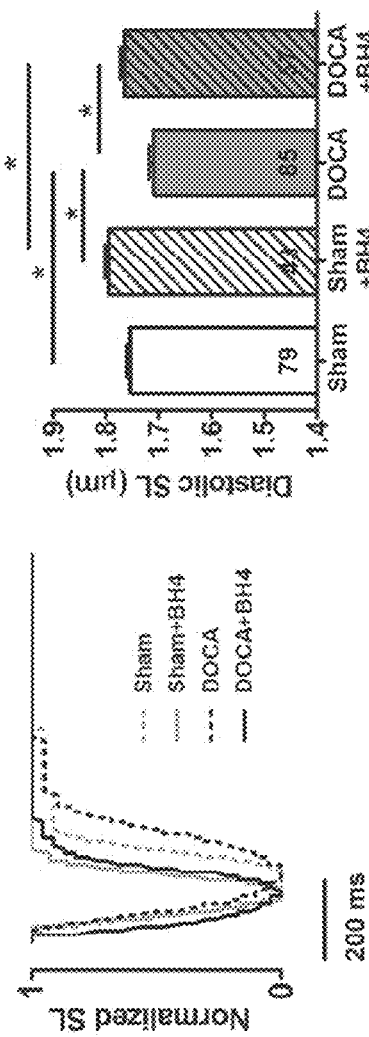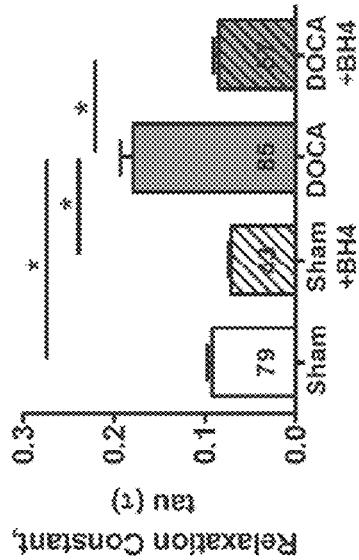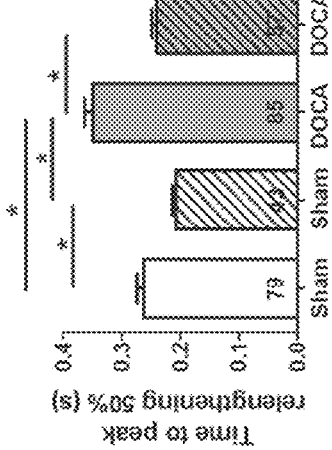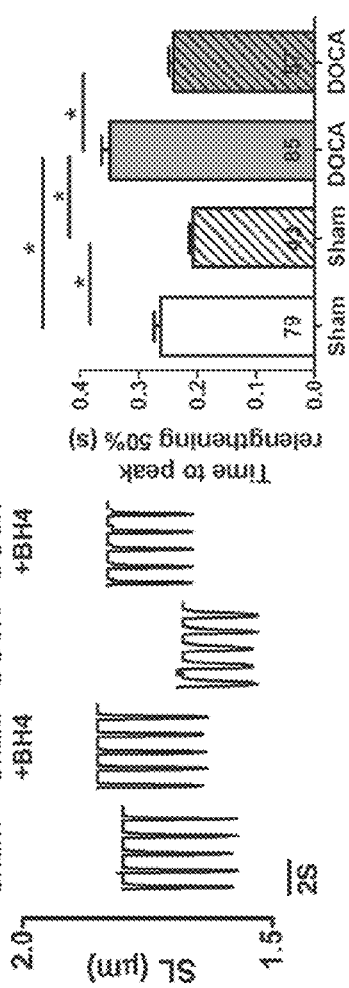
FIG. 2A  FIG. 2B  FIG. 2C
FIG. 2D  FIG. 2E  FIG. 2F

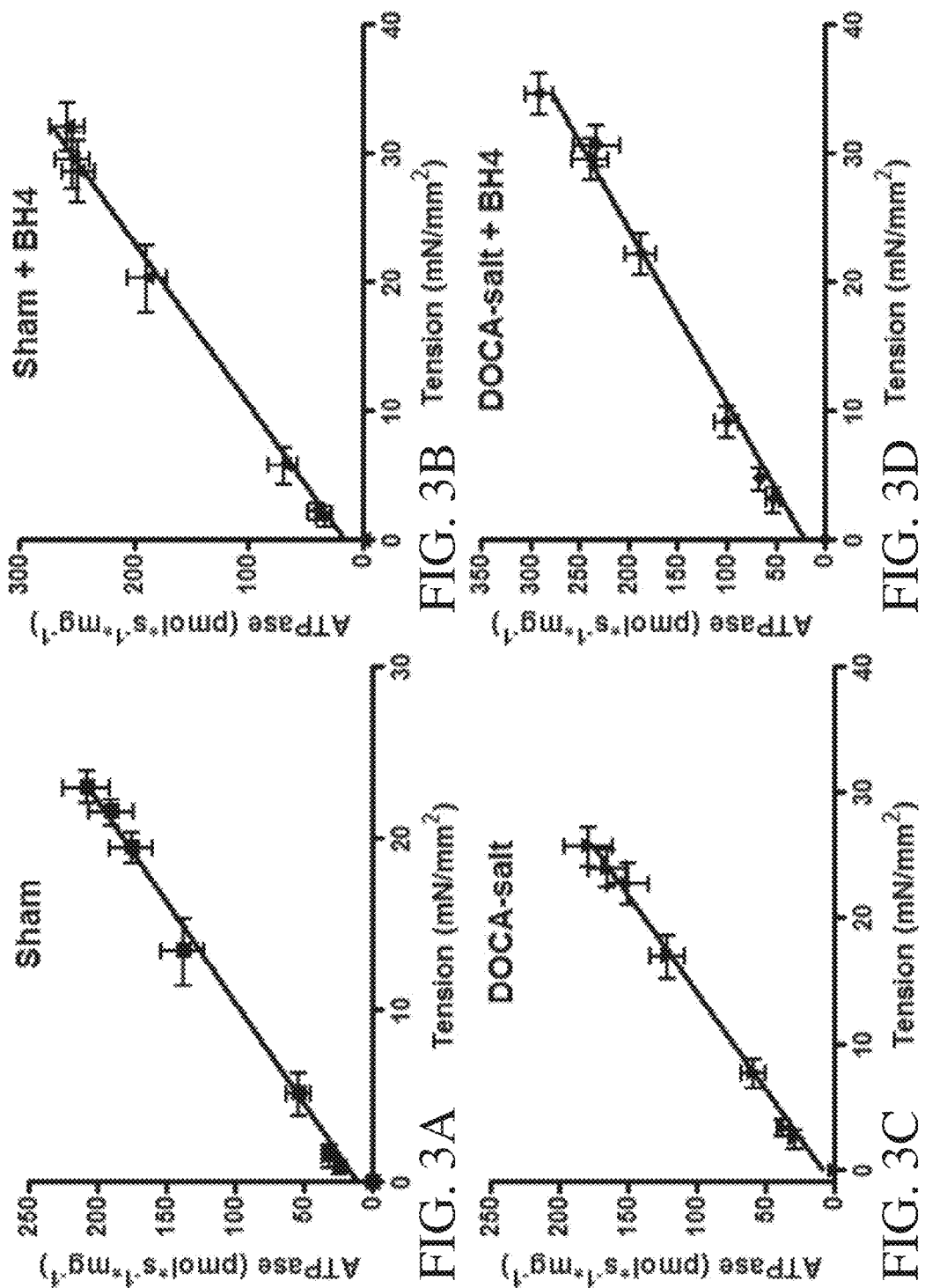

FIG. 5A
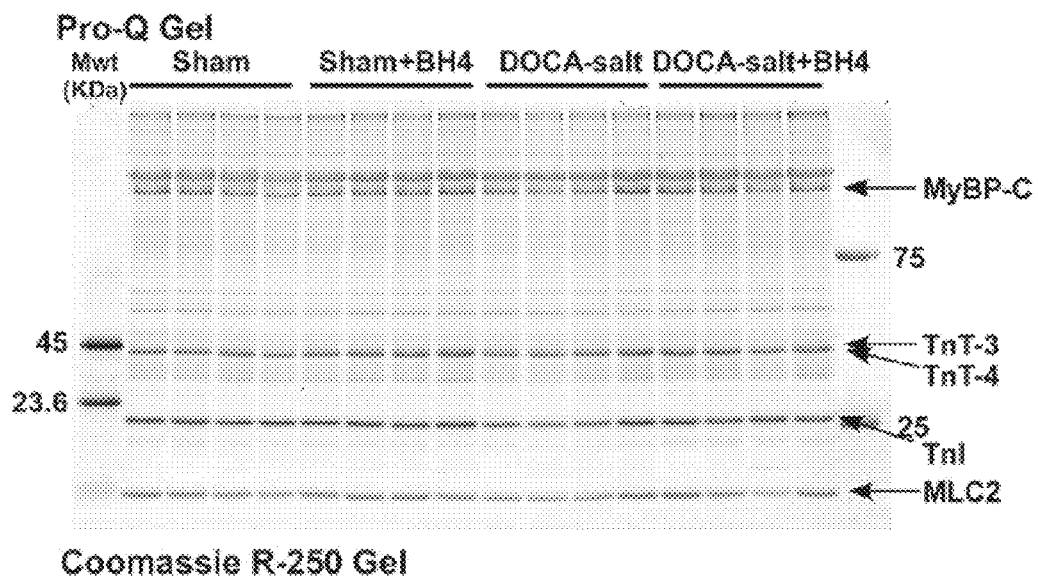
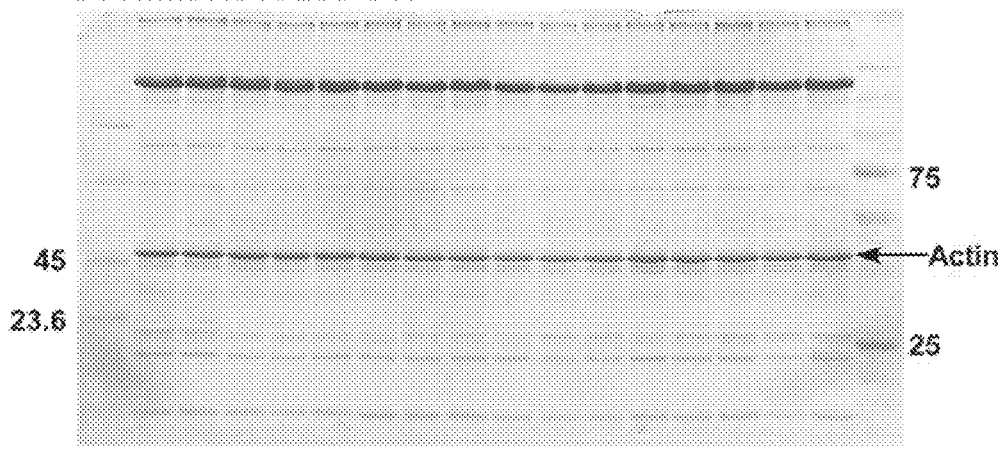
FIG. 5B

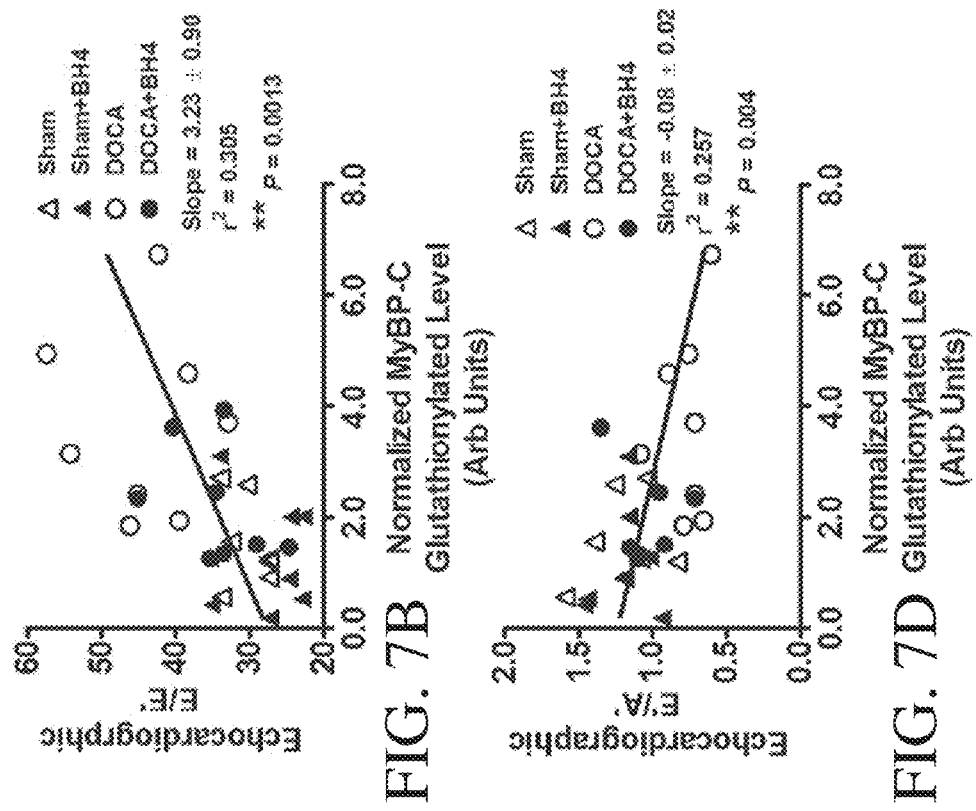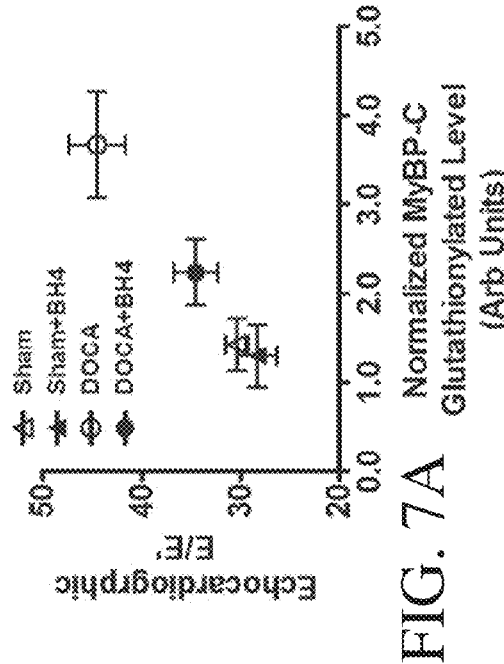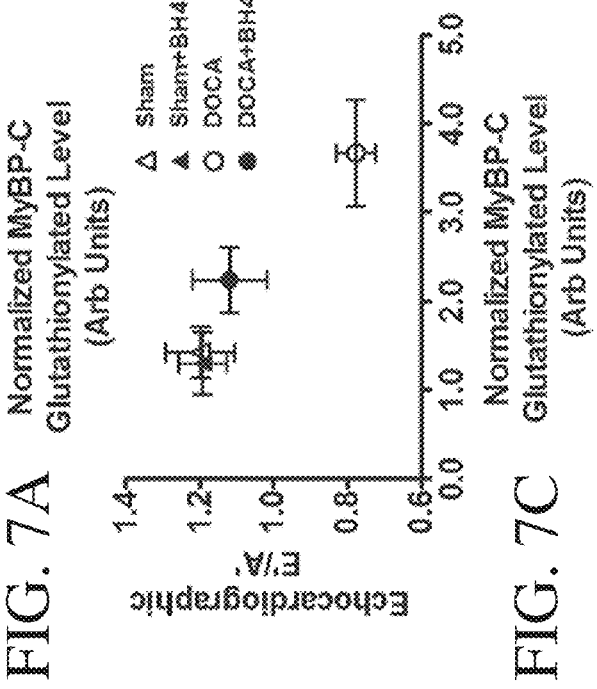
FIG. 7A  FIG. 7B  FIG. 7C  FIG. 7D

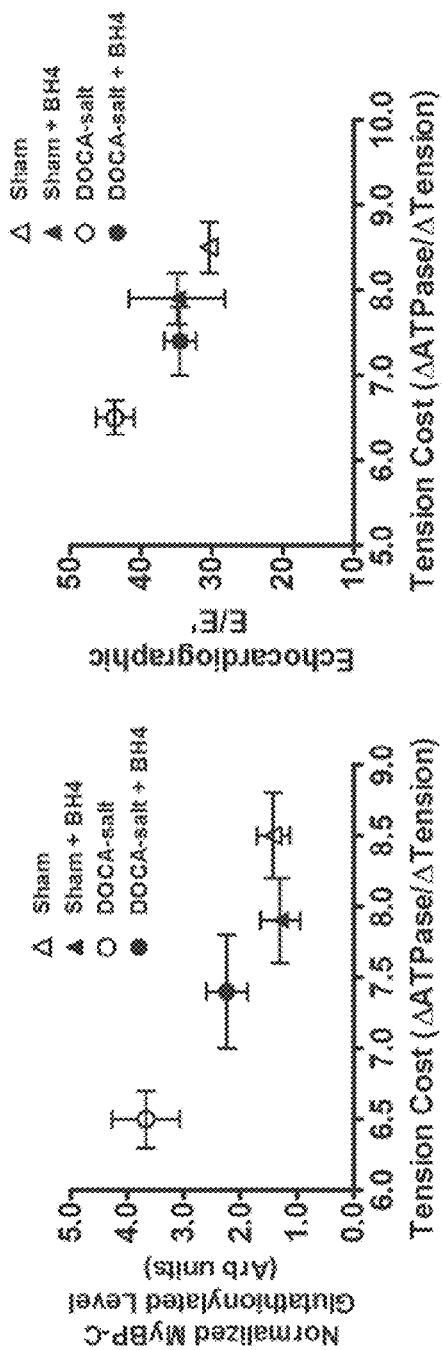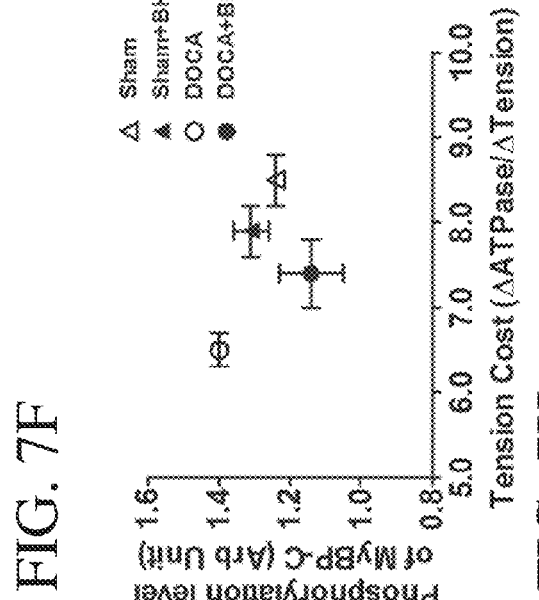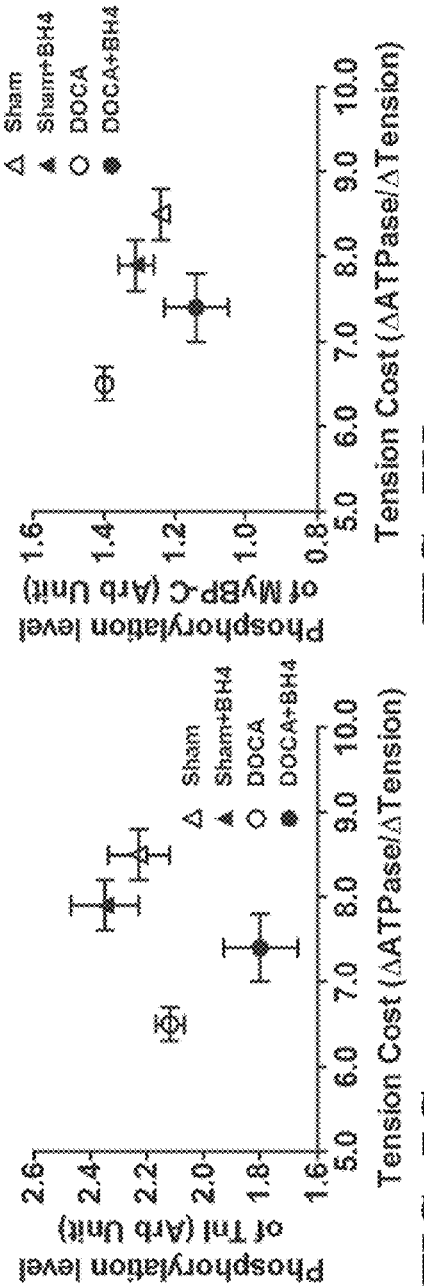
FIG. 7E  FIG. 7F  FIG. 7G  FIG. 7H

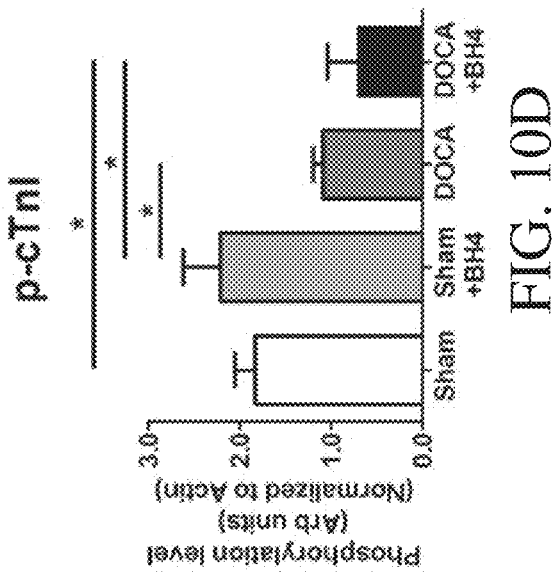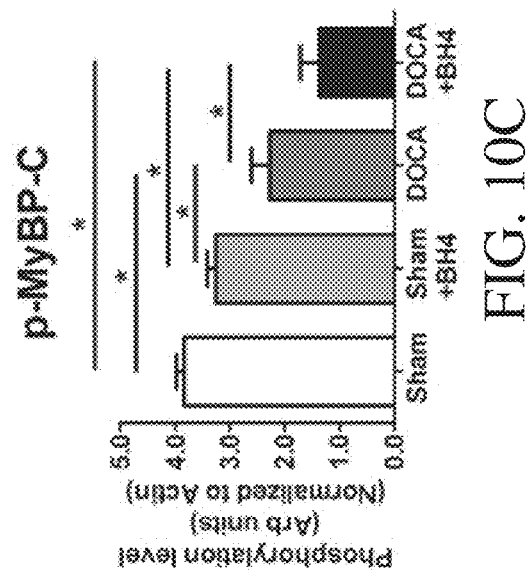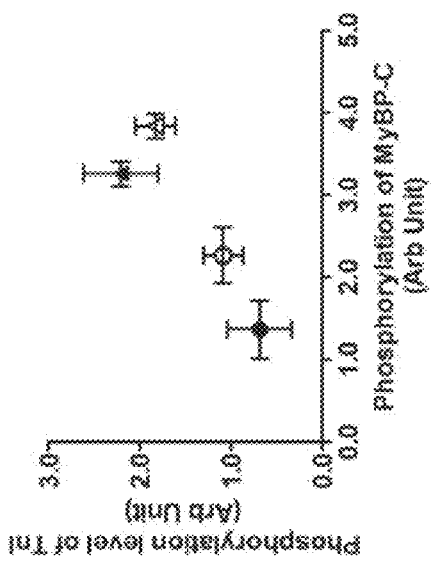
FIG. 10C
FIG. 10D
FIG. 10E

METHOD OF IMPROVING DIASTOLIC DYSFUNCTION

CROSS-REFERENCE TO RELATED APPLICATIONS

This is a continuation-in-part (CIP) application of U.S. application Ser. No. 11/895,883, filed Aug. 27, 2007, which claims the priority benefit of U.S. Provisional Patent Application Ser. No. 60/840,368, filed Aug. 25, 2006, both are hereby incorporated herein in their entirety by reference. This application further claims the priority benefit of U.S. Provisional Patent Application Ser. No. 61/552,500, filed Oct. 28, 2011, which is also hereby incorporated herein in its entirety by reference.

STATEMENT REGARDING FEDERALLY SPONSORED RESEARCH OR DEVELOPMENT

The work leading to the present invention was supported by NIH/NHLBI grants RO1 HL022231, RO1 HL064035, PO1 HL062426 to RJ S, and NIH/NHLBI grants RO1 HL085558, RO1 HL073753, PO1 HL058000, and a Veterans Affairs MERIT grant to SCD. MMM was supported by NIH T32 HL07692-16-20; DMT was supported by University of Illinois at Chicago Center for Clinical and Translational Science (Award Number UL1 RR029879) from the National Center for Research Resources, and by a University of Illinois at Chicago Fellowship. The U.S. Government therefore has certain rights in the invention.

FIELD AND BACKGROUND OF THE INVENTION

The present invention is generally directed to cardiac treatment and therapy, and more particularly to a method of treating, preventing, reversing, or ameliorating diastolic dysfunction.

Hypertension is the most common risk factor for diastolic dysfunction in humans, which can lead to heart failure with preserved ejection fraction (Reference 1). This type of heart failure is increasing, and accounts for significant mortality and healthcare expenditures (References 1 and 2). Current treatments for diastolic dysfunction are inadequate, partially because the mechanism of altered myocardial relaxation is incompletely understood (Reference 3). Nitric oxide (NO) generated by NO synthase (NOS) is a critical modulator of cardiac relaxation (Reference 4), and NO bioavailability is regulated by tetrahydrobiopterin ($BH_4$) (Reference 5).

Under physiological conditions, NOS catalyzes the production of NO from L-arginine to modulate myofilament contractility through mechanisms that are not clear (References 6-9). $BH_4$ depletion, leads to NOS uncoupling (References 5 and 10), the production of superoxide instead of NO, and diastolic dysfunction (References 5 and 11). $BH_4$ supplementation reverses these effects. Recently, I have reported that diastolic dysfunction was characterized by altered myofilament properties and by S-glutathionylation of cardiac myosin binding protein-C (MyBP-C) (Reference 12). S-glutathionylation is an oxidative post-translational modification of protein cysteines by the addition of the anti-oxidant tripeptide glutathione (References 13-15). I tested whether the improvement in diastolic dysfunction with $BH_4$ treatment correlated with changes in myofilament properties and in S-glutathionylation of cardiac MyBP-C.

ASPECTS OF THE INVENTION

The present disclosure is directed to various aspects of the present invention.

One aspect of the present invention is demonstration that by depressing or reducing S-glutathionylation of myosin binding protein-C (MyBP-C), tetrahydrobiopterin ($BH_4$) ameliorates diastolic dysfuntion by reversing a decrease in myofilament cross-bridge kinetics or restorating to normal thereof.

Another aspect of the present invention is demonstration of cardiac relaxation modulation by post-translational modification of myofilament proteins.

Another aspect of the present invention is demonstration that hypertension-induced diastolic dysfunction is characterized by reduced myofilament cross-bridge kinetics that are reversed by $BH_4$, and that the effect of $BH_4$ correlates with a reduction in glutathionylation of MyBP-C, suggesting that this post-translational modification may lead to diastolic dysfunction and that $BH_4$ treatment may work by preventing this oxidative modification.

Another aspect of the present invention is a method of treating, preventing, reversing, or ameliorating diastolic dysfunction, which includes reducing S-glutathionylated myosin binding protein-C (MyBP-C) level by administering to a host in need thereof a therapeutically effective amount of tetrahydrobiopterin ($BH_4$).

Another aspect of the present invention is a method of treating, preventing, reversing, or ameliorating diastolic dysfunction, which includes reversing changes in myofilament cross-bridge kinetics level by administering to a host in need thereof a therapeutically effective amount of tetrahydrobiopterin ($BH_4$).

Another aspect of the present invention is a method of treating, preventing, reversing, or ameliorating diastolic dysfunction, which includes restoring myofilament cross-bridge kinetics to normal level by administering to a host in need thereof a therapeutically effective amount of tetrahydrobiopterin ($BH_4$).

Another aspect of the present invention is a method of treating, preventing, reversing, or ameliorating diastolic dysfunction, which includes modulating post-translational modification of myosin binding protein-C (MyBP-C) level by administering to a host in need thereof a therapeutically effective amount of tetrahydrobiopterin ($BH_4$).

Another aspect of the present invention is a method of treating, preventing, reversing, or ameliorating diastolic dysfunction in a host with manganese superoxide dismutase (MnSOD) deficiency, which includes administering to the host a therapeutically effective amount of tetrahydrobiopterin ($BH_4$).

BRIEF DESCRIPTION OF THE DRAWINGS

One of the above and other aspects, novel features and advantages of the present invention will become apparent from the following detailed description of the non-limiting preferred embodiment(s) of invention, illustrated in the accompanying drawings, wherein:

FIG. 1A illustrates ejection fraction (%, EF) and FIG. 1B illustrates fractional shortening (%, FS) determined in short axix M-mode view. FIG. 1C illustrates mitral inflow pulse-wave Doppler ratio (E/A). FIG. 1D illustrates mitral tissue doppler ratio, E'/A'. FIG. 1E illustrates E/E'. FIGS. 1F-G illustrate representative images from apical four chamber view of pulse-wave (F) and TDI (G). Data was represented mean±SEM. N=7-9 per group. Data were statistically analyzed using JMP statistical software by two-way ANOVA followed by Student's t-test. *$P<0.05$;

FIGS. 2A-I illustrate improved diastolic sarcomere length and relaxation impairement by $BH_4$ treatment. Isolated myocytes from sham, sham+$BH_4$, DOCA-salt and DOCA-salt+$BH_4$ groups were stimulated at 1 Hz recorded by Ionoptix. FIG. 2A illustrates normalized sarcomere trace. FIG. 2B illustrates diastolic resting SL of DOCA-salt group were restored by $BH_4$ treated group. FIG. 2C illustrates fractional shortening. FIG. 2D illustrates sarcomere contraction and relaxation trace. FIG. 2E illustrates peak 50% relengthening time. FIG. 2F illustrates relaxation constant, τ. FIG. 2G illustrates sarcomere contraction/relaxation velocity trace. FIG. 2H illustrates relaxation velocity. FIG. 2I illustrates BDM effect on sarcomere relaxations. BDM (10 mmole/L) were treated on isolated myocytes from Sham, Sham+$BH_4$, DOCA-salt, and DOCA-salt+$BH_4$ groups. DOCA-salt myocytes was increased residual SL by BDM, but there are no difference of residual SK between all groups after BDM treatment. Data was represented mean±SEM. Myocytes n number were indicated as accordingly from 5-7 mice per group. Data were statistically analyzed using JMP statistical software by two-way ANOVA followed by Student's t-test. *$P<0.05$;

FIGS. 3A-D illustrate tension cost for fibers. FIG. 3A illustrates tension cost for fibers from Sham. FIG. 3B illustrates tension cost for fibers from Sham+$BH_4$. FIG. 3C illustrates tension cost for fibers from DOCA-salt. FIG. 3D illustrates tension cost for fibers from DOCA-salt+$BH_4$ groups. Data was represented mean±SEM. N=9-17 fibers per group;

FIG. 4A illustrates maximal tension and $pCa_{50}$ for tension are increased in fibers from DOCA-salt group compared to Sham group. FIG. 4B illustrates maximal ATPase increased in fibers from the DOCA-salt+$BH_4$ group compared to fibers from the DOCA-salt group. Data was represented mean±SEM. N=9-17 fibers per group. Data were statistically analyzed using JMP statistical software by two-way ANOVA followed by Student's t-test. *$P<0.05$;

FIGS. 5A-H illustrate phosphorylation levels of myofilaments proteins. FIG. 5A illustrates representative ProQ. FIG. 5B illustrates coomassie R-250 gel of skinned fiber myofibril proteins. FIG. 5C illustrates phosphorylation levels of myofilament proteins as assessed by ProQ for MyBP-C. FIG. 5D illustrates phosphorylation levels of myofilament proteins as assessed by ProQ for TnT3. FIG. 5E illustrates phosphorylation levels of myofilament proteins as assessed by ProQ for TnT4. FIG. 5F illustrates phosphorylation levels of myofilament protein as assessed by ProQ for TnI. FIG. 5G illustrates phosphorylation levels of myofilament proteins as assessed by ProQ for MLC2. FIG. 5H illustrates phosphorylation levels of myofilament proteins as assessed by ProQ for titin. Data were normalized to actin and statistically analyzed using JMP statistical software by two-way ANOVA followed by Student's t-test. N=4 mice per group;

FIG. 6A illustrates representative Anti-Glutathione gel. FIG. 6B illustrates representative pnceau image. FIG. 6C illustrates MyBP-C glutathionylation level normalized to total lane. Band densitometry data were represented mean±SEM. N=8 mice per group. Data were statistically analyzed using JMP statistical software by two-way ANOVA followed by Student's t-test. *$P<0.05$; and FIGS. 7A-H illustrate the relationship between MyBP-C glutathionylation, diastolic dysfunction, and tension cost. FIGS. 7A-B illustrate echocardiographic parameter-E/E' ratio was positively correlated with normalized MyBP-C glutathionylation level. FIGS. 7C-D illustrate echocardiographic parameter-E'/A' ratio was negatively correlated with normalized MyBP-C glutathionylation level. FIG. 7E illustrates tension cost vs. normalized MyBP-C glutathionylation level. FIG. 7F illustrates tension cost vs. echocardiographic E/E'-negatively correlated. FIGS. 7G-H illustrate tension cost vs. phosphorylation level of TnI (G) and phosphorylation level of MyBP-C(H) from ProQ data. N=7-8 mice per group. * indicates linear regression **$P<0.01$.

FIG. 8A illustrates phosphorylation levels of myofilament proteins as assessed by ProQ for MyBP-C. FIG. 8B illustrates phosphorylation levels of myofilament proteins as assessed by ProQ for TnT3. FIG. 8C illustrates phosphorylation levels of myofilament proteins as assessed by ProQ for TnT4. FIG. 8D illustrates phosphorylation levels of myofilament proteins as assessed by ProQ for TnI. FIG. 8E illustrates phosphorylation levels of myofilament proteins as assessed by ProQ for MLC2. FIG. 8F illustrates phosphorylation levels of myofilament proteins as assessed by ProQ for titin. Data were normalized to total protein and statistically analyzed using JMP statistical software by two-way ANOVA followed by Student's t-test. N=4 mice per group.

FIG. 9A illustrates phosphorylation levels of myofilament proteins as assessed by ProQ for MyBP-C. FIG. 9B illustrates phosphorylation levels of myofilament proteins as assessed by ProQ for TnT3. FIG. 9C illustrates phosphorylation levels of myofilament proteins as assessed by ProQ for TnT4. FIG. 9D illustrates phosphorylation levels of myofilament proteins as assessed by ProQ for TnI. FIG. 9E illustrates phosphorylation levels of myofilament proteins as assessed by ProQ for MLC2. FIG. 9F illustrates phosphorylation levels of myofilament proteins as assessed by ProQ for titin. Data were normalized to MLC1 and statistically analyzed using JMP statistical software by two-way ANOVA followed by Student's t-test. N=4 mice per group.

FIG. 10A-E illustrate phosphorylation levels of MyBP-C and cTnI. FIG. 10A illustrates phosphorylation levels of myofilament proteins as assessed by Western blotting against specific antibodies, Phospho-ser282-MyBP-C, MyBP-C, phospho-Ser23/24-cTnI, and cTnI. FIG. 10B illustrates SDS-PAGE. Densitometry of Western blotting using phospho-Ser282-MyBP-C. FIG. 10C illustrates phospho-Ser23/24-TnI. FIG. 10D illustrates normalized to actin. FIG. 10E illustrates phosphorylation levels from TnI and MyBP-C were correlated. Data were normalized to actin and statistically analyzed using JMP statistical software by two-way ANOVA followed by Student's t-test. N=4 mice per group.

DETAILED DESCRIPTION OF THE PREFERRED EMBODIMENT(S) OF THE INVENTION

Figure 1A:
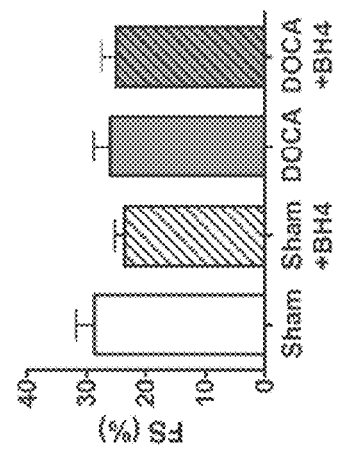
FIGS. 1A-G illustrate thoractic echocargiographic parameters in WT and DOCA-salt mice treated with or without $BH_4$.

A few preferred embodiments of the present invention are described in detail sufficient for one skilled in the art to practice the present invention. It is understood, however, that the fact that a limited number of preferred embodiments are described herein does not in any way limit the scope of the present invention.

Recently, I reported that hypertension-induced diastolic dysfunction was accompanied by cardiac $BH_4$ depletion, NOS uncoupling, a depression in myofilament cross-bridge kinetics, and S-glutathionylation of myosin binding protein C (MyBP-C). I hypothesized that the mechanism by which $BH_4$ ameliorates diastolic dysfunction is by preventing glutathionylation of MyBP-C and thus reversing changes of myofilament properties that occur during diastolic dysfunction. I used the deoxycorticosterone acetate (DOCA)-salt mouse model, which demonstrates mild hypertension, myocardial oxidative stress, and diastolic dysfunction.

As noted in more detail below, the mice were divided into two groups that received control diet and two groups that received $BH_4$ supplement for 7 days after developing diastolic dysfunction at post-operative day 11. Mice were assessed by echocardiography. Left ventricular papillary detergent-extracted fiber bundles were isolated for simultaneous determination of force and ATPase activity. Sarcomeric protein glutathionylation was assessed by immunoblotting. DOCA-salt mice exhibited diastolic dysfunction that was reversed after $BH_4$ treatment. Diastolic sarcomere length (DOCA-salt 1.70±0.01 vs. DOCA-salt+$BH_4$ 1.77±0.01 μm, P<0.001) and relengthening (relaxation constant, τ, DOCA-salt 0.28±0.02 vs. DOCA-salt+$BH_4$ 0.08±0.01, P<0.001) were also restored to control by $BH_4$ treatment. $pCa_{50}$ for tension increased in DOCA-salt compared to sham, but reverted to sham levels after $BH_4$ treatment. Maximum ATPase rate and tension cost (ΔATPase/ΔTension) decreased in DOCA-salt compared to sham, but increased after $BH_4$ treatment. Cardiac MyBP-C glutathionylation increased in DOCA-salt compared to sham, but decreased with $BH_4$ treatment. MyBP-C glutathionylation correlated with the presence of diastolic dysfunction.

My results herein suggest that by depressing S-glutathionylation of MyBP-C, $BH_4$ ameliorates diastolic dysfunction by reversing a decrease in cross-bridge turnover kinetics. These data provide evidence for modulation of cardiac relaxation by post-translational modification of myofilament proteins.

Here, I demonstrate that oral administration of $BH_4$ improves diastolic dysfunction, reverses the changes in actin-myosin cross-bridge cycling, and decreases S-glutathionylated MyBP-C. My results support the hypothesis that oxidative post-translational modifications and associated modulation of myofilament properties is a molecular mechanism for diastolic dysfunction.

Methods

All protocols were in accordance with the guidelines of the Animal Care and Use Committee of the University of Illinois and comply with the laws of the United States of America.

EXAMPLE I

Generation of DOCA-Salt Mouse Model

Previously, I have shown that the DOCA-salt mouse model leads to mild hypertension, NOS uncoupling, myocardial oxidative stress, and diastolic dysfunction (Reference 10). A gradual and mild elevation in blood pressure was induced by unilateral nephrectomy, subcutaneous implantation of a controlled release deoxycorticosterone acetate (DOCA) pellet (0.7 mg/d; Innovative Research of America, Sarasota, Fla.), and substituting drinking water with 1.05% saline. Control animals underwent a sham operation, had placebo pellet implantation, and received water without salt.

Administration of $BH_4$

Mice were divided into two groups which received a control diet (sham N=7; DOCA-salt N=10) and two groups which received a $BH_4$ supplemental diet of 5 mg $BH_4$/day (Research Diets Inc, New Brunswick, N.J.; sham+$BH_4$ N=8; DOCA-salt+$BH_4$ N=8). The supplemental diet began on day 11 after surgery, and continued until day 18, when the mice were analyzed and sacrificed.

Transthoracic Echocardiography

Mitral pulse wave Doppler flow and tissue Doppler imaging (TDI) were performed using the Vevo 770 high-resolution in vivo imaging system (Visual Sonics, Toronto, Canada) (Reference 10). Mice were anesthetized with 1-1.5% isoflurane until a heart rate of around 350-390 beats/min was achieved because measures of diastolic function are sensitive to heart rate and loading conditions. M-mode images in the parasternal long axis and the left ventricle (LV) short-axis views at the mid-papillary level were taken. Measurements were averaged from five consecutive beats during expiration. The images for each mouse were recorded for at least 5 s (30-40 cardiac cycles) from which three to five representative cycles with the highest quality imaging were selected. Percent fractional shortening (% FS) was calculated as 100×(LVEDd)−(LVESd)/(LVEDd) and percent LV ejection fraction (% EF) was calculated as $100 \times [(7/2.4+LVEDd) \times LEDd^3]−[(7/2.4+LVESd) \times LVESd^3]/[(7/2.4+LVEDd) \times LEDd^3]$. Doppler measurements were made at the tips of the mitral leaflets for diastolic filling profiles in the apical four-chamber view. Mitral inflow velocities, peak early (E) and late (A) were measured by conventional pulsed-wave Doppler. TDI was used to determine the mitral annulus longitudinal velocities (Sm, E', and A') (Reference 10). Baseline images before treatment were acquired to confirm diastolic dysfunction in DOCA-salt mice. Subsequently, the mice were fed with $BH_4$, followed by echocardiography at day 18.

Cardiomyocyte Studies

Ventricular myocytes were isolated as previously described (Reference 10). Hearts were excised from anesthetized mice, perfused with buffer (in mmol/L: NaCl 113, KCl 4.7, $Na_2HPO_4$ 0.6, $KH_2PO_4$ 0.6, $MgSO_4$ 1.2, Phenol Red 0.032, $NaHCO_3$ 12, $KHCO_3$ 10, HEPES 10, Taurine 30, 2-3-butanedione monoxime 10) and digested with collagenase II (Worthington Biochemical Co. Lakewood, N.J.) for 7-8 min with 37° C. perfusion. Cardiomyocytes were washed with control buffers (in mmol/L: NaCl 133.5, KCl 4, $Na_2HPO_4$ 1.2, HEPES 10, $MgSO_4$ 1.2 and 0.1% Bovine serum albumin) with serially increasing $Ca^{2+}$ concentrations (0.2, 0.5, and 1 mmol/L). Then, myocytes were maintained in MEM medium (modified Eagle's medium with 1% insulin-transferrin-selenium, 0.1% bovine serum albumin, 1% glucose, and 1% penicillin/streptomycin) in a 95% $O_2$/5% $CO_2$ incubator at 37° C. until use.

The mechanical properties of the cardiomyocytes were assessed using an IonOptix Myocam System (IonOptix Inc., Milton, Mass.) as described previously (Reference 12). Unloaded cardiomyocytes isolated from each group of mice were placed on a glass slide and allowed to adhere for 5 min, then imaged with an inverted microscope and perfused with a normal Tyrode's buffer (in mmol/L: 133 NaCl, 5.4 KCl, 5.3 $MgCl_2$, 0.3 $Na_2PO_4$, 20 HEPES, 10 glucose, pH 7.4) containing 1.2 mmol/L calcium at 37° C. with a temperature controller. Cardiomyocytes were paced with 10 V, 4 ms square wave pulses at 1.0 Hz, and sarcomere shortening and relengthening were assessed using the following indices: diastolic sarcomere length (SL), peak fractional shortening (FS, %), the prolonged relaxation time constant τ($a_0+a_1 e^{t/\tau}$, t=time), relengthening time (s), and maximum relaxation velocity (dL/dt).

2,3-Butanedione monoxime (BDM), a cross-bridge inhibitor, was used to measure residual sarcomere length. BDM inhibits the $Ca^{2+}$ regulated attachment of the cross-bridges and force-generation of the attached cross-bridges (Reference 16). Isolated single myocytes were loaded on an chamber and perfused with BDM (10 mM) in Tyrode's solution at 37° C. Sarcomere length was again measured while the myocytes were field-stimulated as described above.

Dissection of Left Ventricular Papillary Muscles and Preparation of Skinned Fibers Mice were anesthetized with pentobarbital (50 mg/kg IP), and the hearts were rapidly excised and rinsed in ice-cold relaxing solution (pH 7.0) composed of (in mM) 10 EGTA, 41.89 K-Prop, 6.57 $MgCl_2$, 100 BES, 6.22 ATP, 5 Na azide, and 10 creatine phosphate. The solution also contained 1 μg/mL leupeptin, 2.5 μg/ml pepstatin A, and 50 μM phenylmethylsulfonyl fluoride. Left ventricular papillary muscles were dissected and fiber bundles were prepared as previously described (Reference 17). The fiber bundles were extracted overnight in relaxing solution plus 1% Triton X-100 at 4° C.

Simultaneous Determination of Force and ATPase Activity in Detergent-Extracted Cardiac Fiber Bundles Force and ATPase rate were measured simultaneously as previously described (Reference 17) using an experimental apparatus also previously described (Reference 18). The fiber bundles were mounted between a force transducer and displacement motor using aluminum T-clips, and the sarcomere length was set to 2.2 μm using He—Ne laser diffraction (Reference 19). The width and diameter were each measured at three points along the fiber bundle. Force per cross-sectional area was used to determine tension. The fiber was initially contracted at a saturating calcium concentration (pCa 4.5) and sarcomere length was again adjusted to 2.2 μm. Sarcomere length remained constant throughout the rest of the experiment.

ATPase activity was measured at 20° C. as previously described (References 17 and 20) and calibrated with rapid injections of ADP (0.5 nmol) with a motor-controlled syringe. The fiber was placed in relaxing solution for 2 min, then in the pre-activation solution for 2-3 min each time before being placed in the activating solution for 1-2 min (until stabilization of force) and then quickly returned to the relaxing solution. Various contraction-relaxation cycles were carried out using different ratios of total calcium concentration to total EGTA concentration. The final contraction was again at pCa 4.5.

Analysis of Sarcomeric Protein Phosphorylation

In one series of experiments, I employed Pro-Q Diamond (Invitrogen) gel stain to determine changes in phosphorylation of myofilament proteins. I also employed site specific antibodies for MyBP-C (anti-phospho-peptide-Ser282) and for cTnI (anti-phopho-Ser23/Ser24). Detailed methods are presented below.

Analysis of Sarcomeric Protein Glutathionylation by Western Immunoblotting

Myofibrils were prepared from DOCA-salt and sham model hearts, and pellets were solubilized in a non-reducing 2× Laemmli buffer (4% SDS, 20% glycerol, 0.004% bromophenol blue, and 0.125 M Tris HCl pH 6.8). 25 mM N-ethylmaleimide (NEM) was added to the standard rigor buffer with Triton X-100, the standard rigor wash buffer and the 2× Laemmli buffer. (Reference 21). Using the protein concentration determined from an RC-DC (Bio-Rad) assay, 40 pg of total protein was applied to a 12% SDS-PAGE gel and transferred onto a 0.2 μm PVDF membrane. The blot was blocked in 5% nonfat dry milk with 2.5 mM NEM for 1 h. Anti-glutathione mouse monoclonal primary antibody (Virogen) was used at 1:1000 dilution along with anti-mouse HRP-conjugated secondary antibody (Sigma) at 1:100,000 dilution to detect for S-glutathionylation (Reference 22). Optical density of the bands was measured with ImageQuant TL (GE Healthcare) and exported to Excel for further analysis.

Statistical Analysis

Echocardiography, sarcomere shortening, skinned fiber tension, and ATPase measurements, as well as post-translational modifications of myofilament proteins, were statistically analyzed by two-way ANOVA followed by student's t test using JMP statistical software. Analysis of the relation between $Ca^{2+}$ and tension or ATPase activity was fitted using a modified Hill equation as described previously [20]. Analysis of the relation between MyBP-C glutathionylation and echocardiographic, E/E' ratio was correlated in linear regression analysis. A value of $P<0.05$ was considered significantly different. Data are presented as means±SEM.

Analysis of Sarcomeric Protein Phosphorylation by Pro-Q Diamond Phosphoprotein Gel Stain Pro-Q Diamond (Invitrogen) gel stain was used to detect changes in phosphorylation states of the proteins. Myofibrils were prepared from DOCA-salt and sham models of the mice hearts, and pellets were solubilized in a non-reducing 2× Laemmli buffer (4% SDS, 20% glycerol, 0.004% bromophenol blue, and 0.125 M Tris HCl pH 6.8) (Reference 21). 25 mM N-ethylmaleimide (NEM) was added to the standard rigor buffer with Triton X-100, the standard rigor wash buffer and the 2× Laemmli buffer. An RC-DC assay (Bio-Rad) was used to determine protein concentrations. Samples were diluted at 1:1 ratio in reducing sample buffer (8 M urea, 2 M thiourea, 0.05 M tris pH 6.8, 75 mM DTT, 3% SDS, and 0.05% bromophenol blue) (Reference 41) and approximately 10 pg of protein was loaded on to a 12% resolving 1D SDS-PAGE gel. (References 42 and 43). The gels were stained and destained with Pro-Q Diamond according to the manufacturer's recommendations prior to imaging with a Typhoon 9410 scanner (GE Healthcare). Coomassie R-250 staining was used to normalize protein load to both MLC1 and the whole lane. Optical density of the proteins was determined using ImageQuant TL (GE Healthcare) software and results were exported to Excel for further analysis.

Analysis of Sarcomeric Protein Phosphorylation by Western Immunoblotting

Myofibrils were prepared from DOCA-salt and sham mice hearts with or without $BH_4$ treatment (Reference 21) and pellets were solubilized in a reducing 2× Laemmli buffer (4% SDS, 20% glycerol, 0.004% bromophenol blue, 75 mM DTT and 0.125 M Tris HCl pH 6.8). An RC-DC assay (Bio-Rad) was used to determine protein concentrations. Samples were diluted at 1:1 ratio in reducing sample buffer (8 M urea, 2 M thiourea, 0.05 M tris pH 6.8, 75 mM DTT, 3% SDS, and 0.05% bromophenol blue) (Reference 41). Approximately 10 μg of protein was applied on to a 12% resolving 1D SDS-PAGE gel (References 42 and 43) and transferred onto a 0.2 μm PVDF membrane. The blot was blocked in 5% nonfat dry milk for 1 h. Anti-phospho-ser282-MyBP-C rabbit polyclonal antibody antibody (ENZO) and MyBP-C rabbit anti-doby (Santa Cruz) was used at 1:1000 dilution along with anti-rabbit HRP-conjugated secondary antibody (Sigma) at 1:100,000 dilution to detect serine 282 site specific phosphorylation of MyBP-C. Anti-phospho-ser23/24-cTn1 rabbit polyclonal antibody (Cell Signaling) was used at 1:1000. Coomassie R-250 staining was used to normalize protein load to both actin and the whole lane. Optical density of the bands was measured with Image J and exported to Excel for further analysis.

Results

Improvement in Diastolic Function with $BH_4$

Figure 1B:
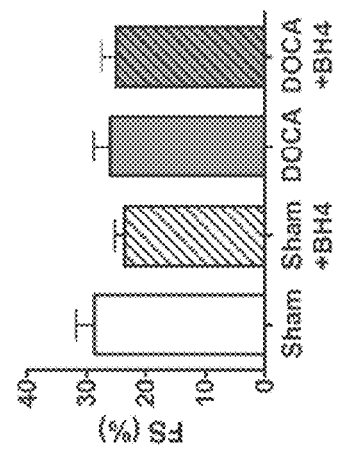

Ten days after surgery, I employed echocardiography to characterize the diastolic dysfunction. Treatment with a $BH_4$ supplemental diet was begun on post-operative day 11, and echocardiography was repeated on postoperative day 18. The results can be seen in FIG. 1 and Table 1 (below). Seven days of $BH_4$ administration in sham and DOCA-salt mice did not affect LV ejection fraction (FIG. 1A) or fractional shortening (FIG. 1B).

Figure 1C:
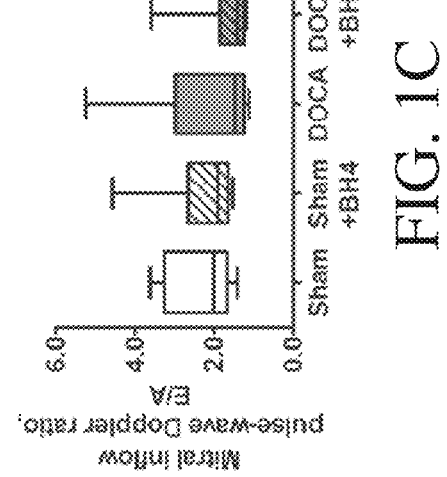
Figure 1D:
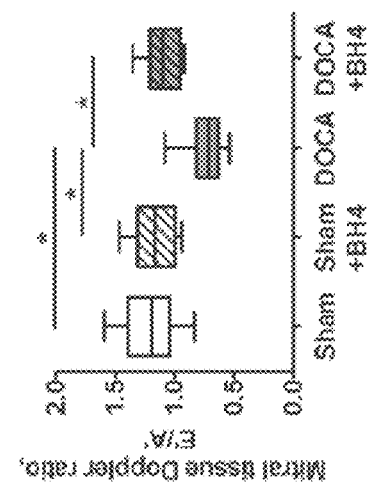
Figure 1E:
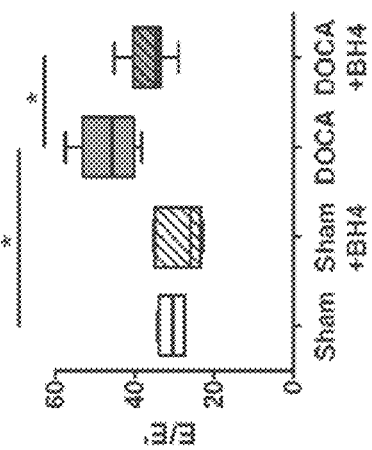
Figure 1F:
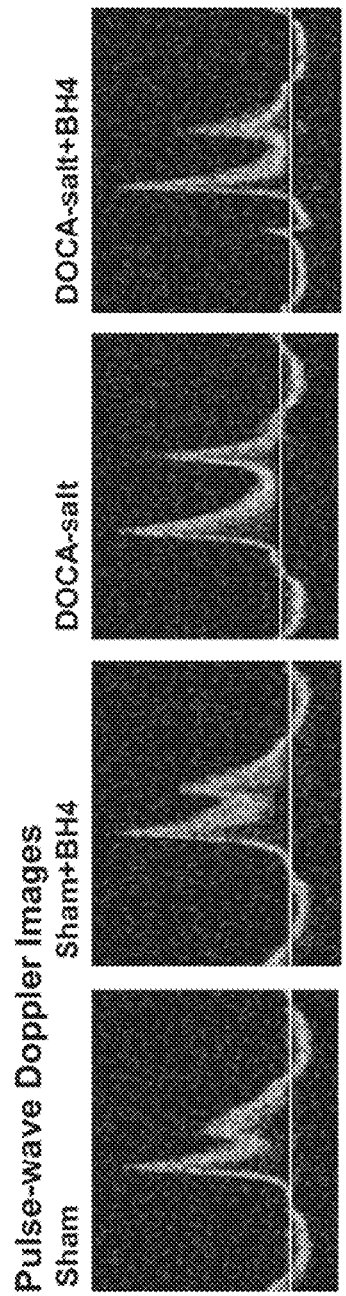
Figure 1G:
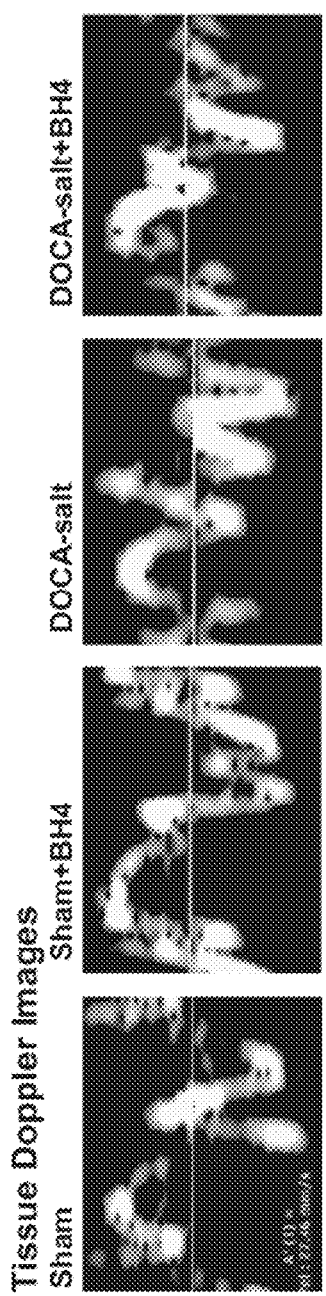

Mitral Doppler flow was measured at comparable heart rates (~average 370 beats/min) in all mice (Reference 10). As I have reported in this model, mitral E velocity, A velocity, and the E/A ratio were not significantly changed in all groups (FIGS. 1C and 1F). Nevertheless, mitral tissue Doppler E' was significantly decreased in the DOCA-salt mice indicating a pseudo-normal diastolic dysfunction stage. The ratio of E'/A' was significantly decreased in DOCA-salt mice and restored with $BH_4$ treatment (DOCA-salt+$BH_4$, 1.12±1.10 vs. DOCA-salt, 0.74 ±0.05, P <0.05). The sham and sham+$BH_4$ groups did not show any significant differences in E'/A' (FIGS. 1D and 1G). The E/E' ratio, a measure of left atrial pressure, was significantly increased in DOCA-salt mice, and restored to the control level after $BH_4$ administration (FIG. 1E, DOCA-salt +$BH_4$, 34.5±2.2 vs. DOCA-salt, 43.7±2.7, P <0.05).

Improvement in Cardiomyocyte Parameters of Relaxation with $BH_4$

Figure 2G:
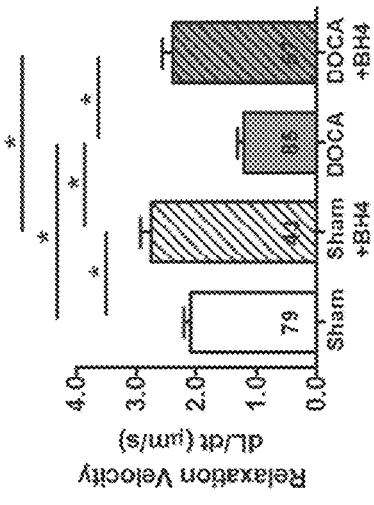
Figure 2H:
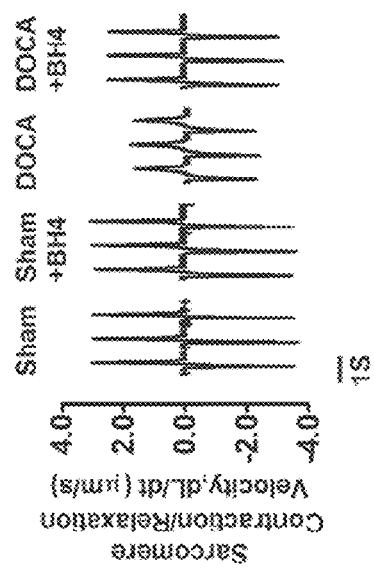

To confirm diastolic relaxation impairment in the model, I isolated single myocytes from each group and measured sarcomeric contraction and relaxation function, as seen in FIG. 2 and Table 2 (below). Sarcomere length was shortened in DOCA-salt mice and restored after $BH_4$ treatment (FIGS. 2A-D). Fractional shortening was not changed in all groups (FIG. 2C). On the other hand, the relaxation constant (τ), 50% relengthening time were significantly increased in DOCA-salt mice and returned to their normal levels after $BH_4$ treatment (FIGS. 2E-F). The reduced relaxation rate in DOCA-salt mice reverted to control levels with $BH_4$ treatment (FIGS. 2G-H).

Figure 2I:
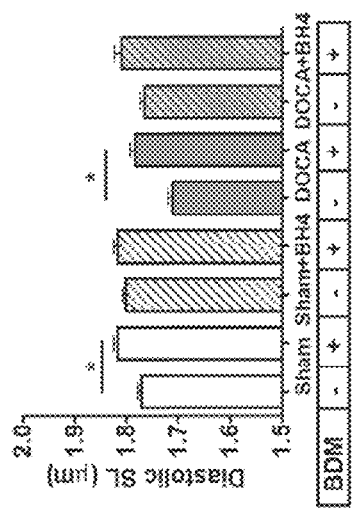

To determine whether increased diastolic tension could be explained by active cross-bridge cycling, I treated the myocytes with BDM, a non-competitive inhibitor of active force-generation (Reference 16). Treatment of isolated myocytes with BDM (10 mM) increased residual sarcomere length in the sham and DOCA-salt groups. Treatment of either group with $BH_4$ resulted in significant relaxation as measured by sarcomere length. After $BH_4$ treatment, BDM had no effect, suggesting that $BH_4$ facilitated cross-bridge dissociation (FIG. 2I).

Myofilament Properties Altered by $BH_4$

Figure 4A:
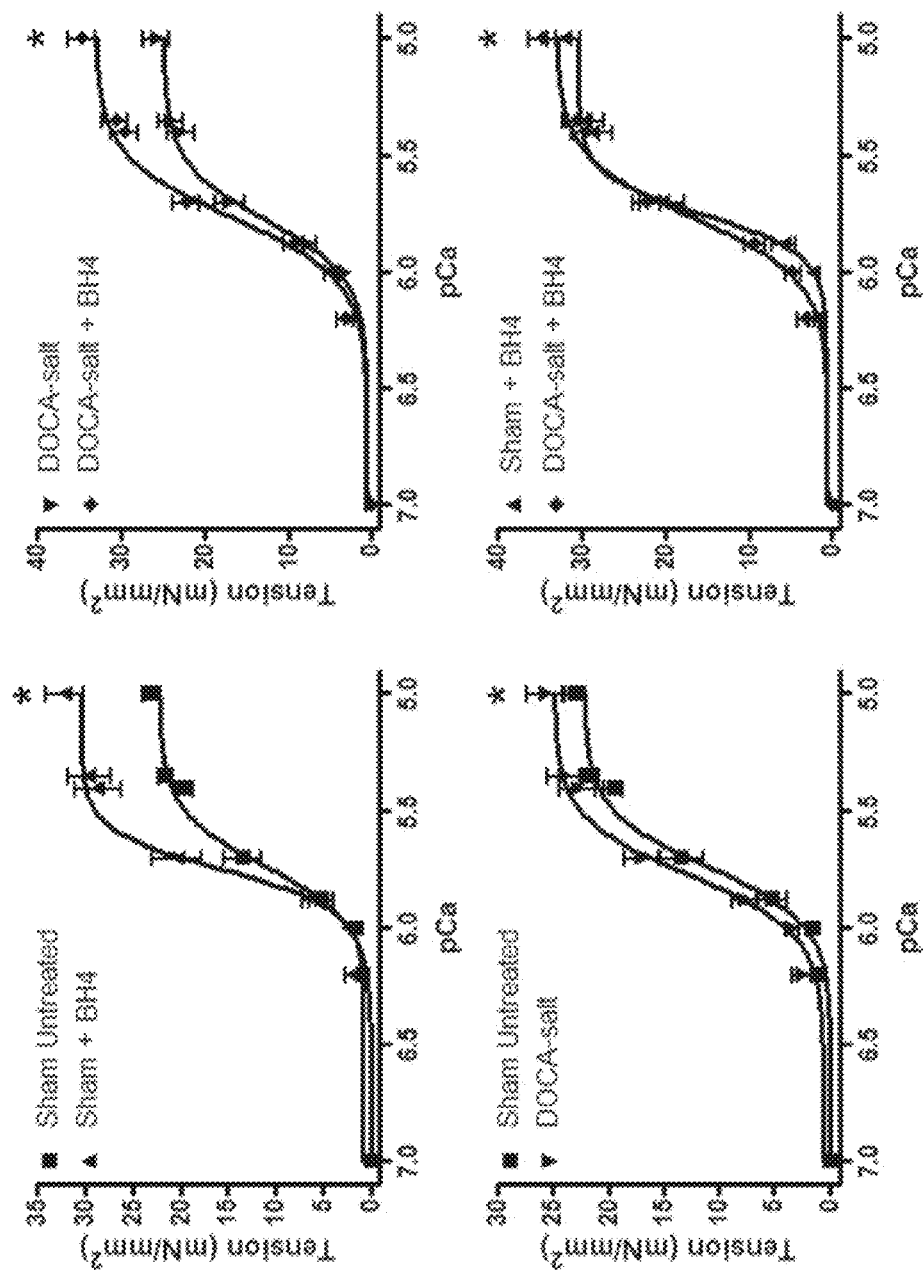
FIGS. 4A-B illustrate $Ca^{2+}$-sensitivity and ATPase of skinned fiber preparations.
Figure 4B:
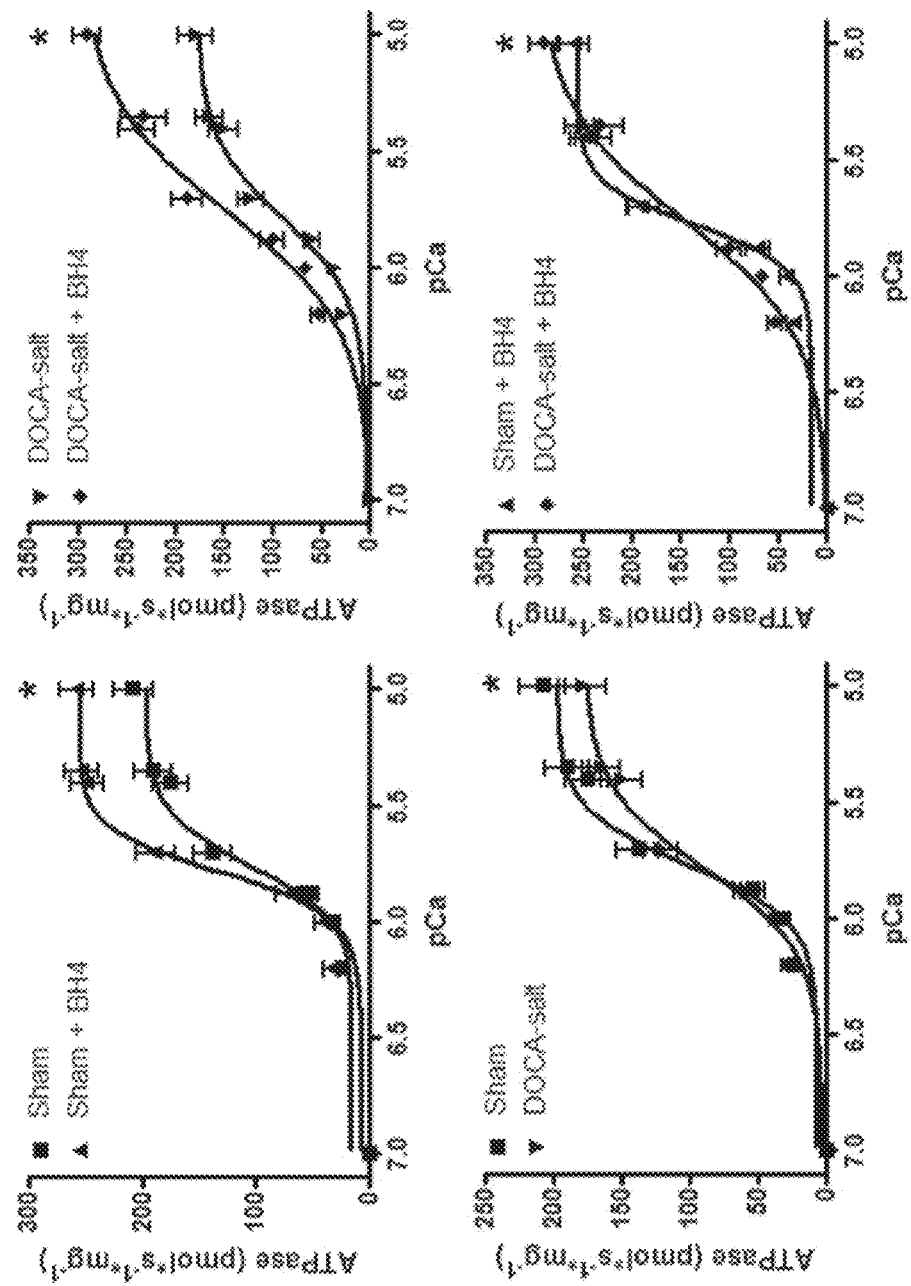
Figure 5C:
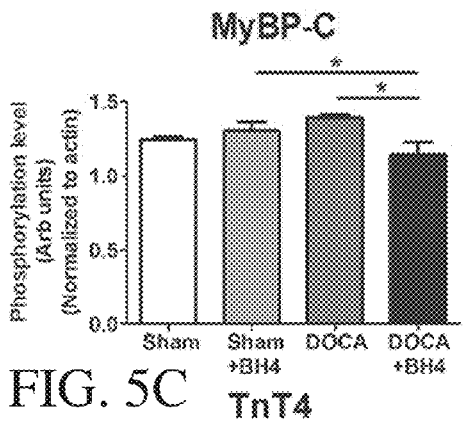
Figure 5D:
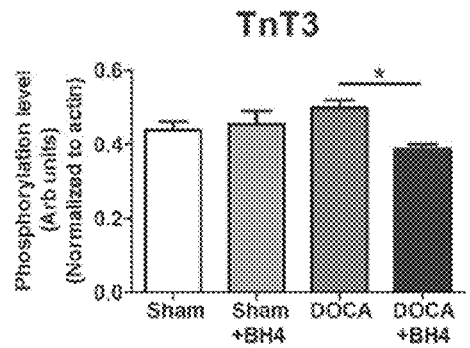
Figure 5E:
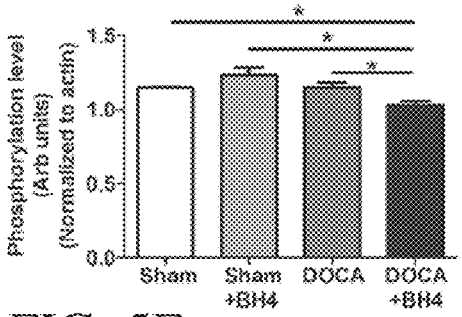
Figure 5F:
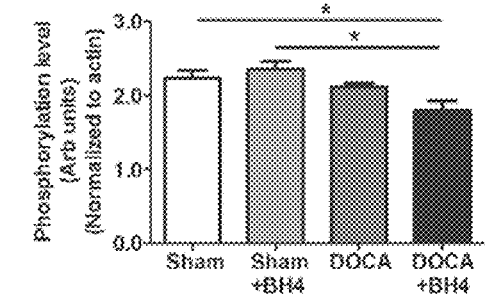
Figure 5G:
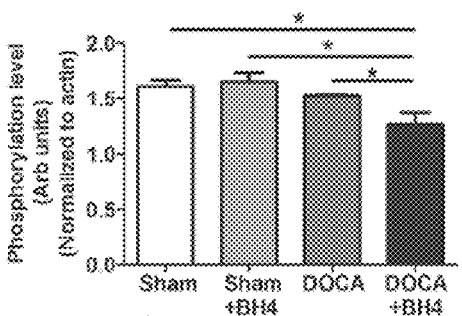
Figure 5H:
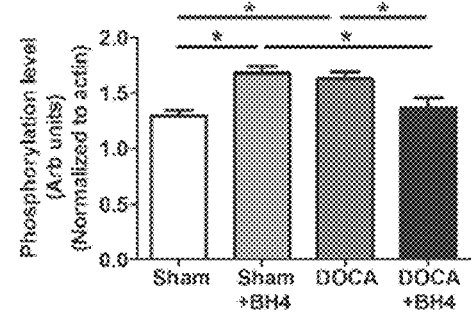

In order to assess the relation between myocardial diastolic dysfunction and changes in myofilament properties, I performed analysis of tension and ATPase activity in skinned fiber preparations (FIGS. 3 and 4). My results indicate that tension cost (ΔATPase/Δtension) of skinned fibers from the DOCA-salt group (6.5±0.2) was significantly (P<0.05) reduced compared to shams (8.5±0.3) demonstrating that a slowing of cross bridge kinetics was responsible for diastolic dysfunction. Tension cost in fibers from the DOCA-salt+$BH_4$ group was increased (7.4±0.4, P<0.05) compared to the DOCA-salt group to a level not significantly different from either sham group (FIG. 3, and Table 3 - below).

Maximum ATPase rate was also significantly reduced in DOCA-salt mice. This was accompanied by modest changes in maximum tension, $pCa_{50}$ for tension and ATPase rate. $BH_4$ treatment increased maximum tension and ATPase rates in both sham and DOCA-salt mice, again with modest changes in $pCa_{50}$ and significant changes in tension cost that varied in DOCA-salt versus sham mice. (FIG. 4, and Table 3-below).

Myosin Binding Protein C Post-Translational Modifications

In one set of experiments, I determined potential modifications in phosphorylation of myofilament proteins employing Pro-Q diamond phospho-protein gel stain. With $BH_4$ treatment in the DOCA-salt mice, there was a decrease in phosphorylation of major myofialment proteins, MyBP-C, TnT3, cTnT4, MLC2 and titin, and no change in cTnI phosphorylation. The decreases in phosphorylation would tend to slow cross-bridge kinetics or increase diastolic stiffness, and thus are not likely to account for the reversal of effects of DOCA-salt on diastolic dysfunction with BH4 treatment. To further test this conclusion, I determined the level of site-specific phosphorylation changes in both MyBP-C and cTnI (FIGS. 10A-E). Phosphorylation at Ser282 of MyBP-C was decreased in myofilaments from hearts of DOCA-salt mice compared to shams. $BH_4$ further reduced phosphorylation of MyBP-C at Ser282 in myofilaments from DOCA-salt mice, but did not significantly alter phosphorylation at this residue in sham myofilaments. Phosphorylation of cTnI at Ser23/24 was significantly reduced in myofilaments from DOCA-salt mice compared to sham, but was not significantly changed by BH4 in either from DOCA-salt or sham mice. Decreases in phosphorylation of MyBP-C and TnI, have been previously demonstrated to slow cross-bridge kinetics (References 23 and 24). Thus, one could speculate that the decrease in phosphorylation of these two proteins that I observe in hearts from DOCA-salt mice may contribute to the impaired relaxation. However, I did not observe a reversal of phosphorylation of these two proteins in the presence of BH4 when diastolic function had recovered. Therefore, my results indicate that while the lower phosphorylation MyBP-C and cTnI may play a role in diastolic dysfunction, changes in S-glutathionylation of MyBP-C correlates with changes in diastolic function mediated by $BH_4$ in this model.

Figure 6A:
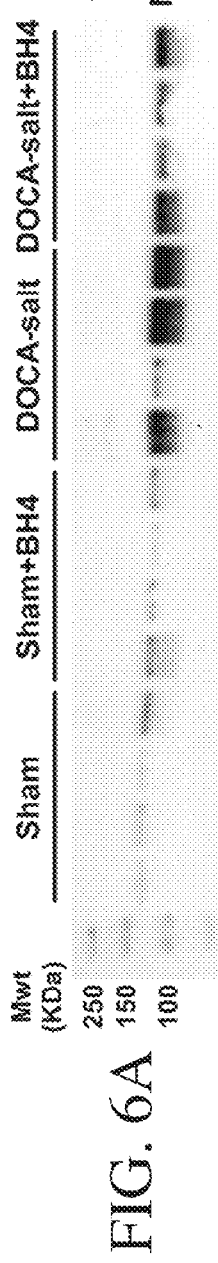
FIGS. 6A-C illustrate glutathionylation levels of MyBP-C.
Figure 6B:
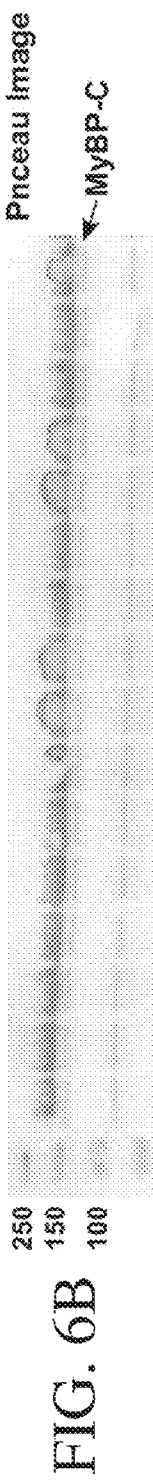
Figure 6C:
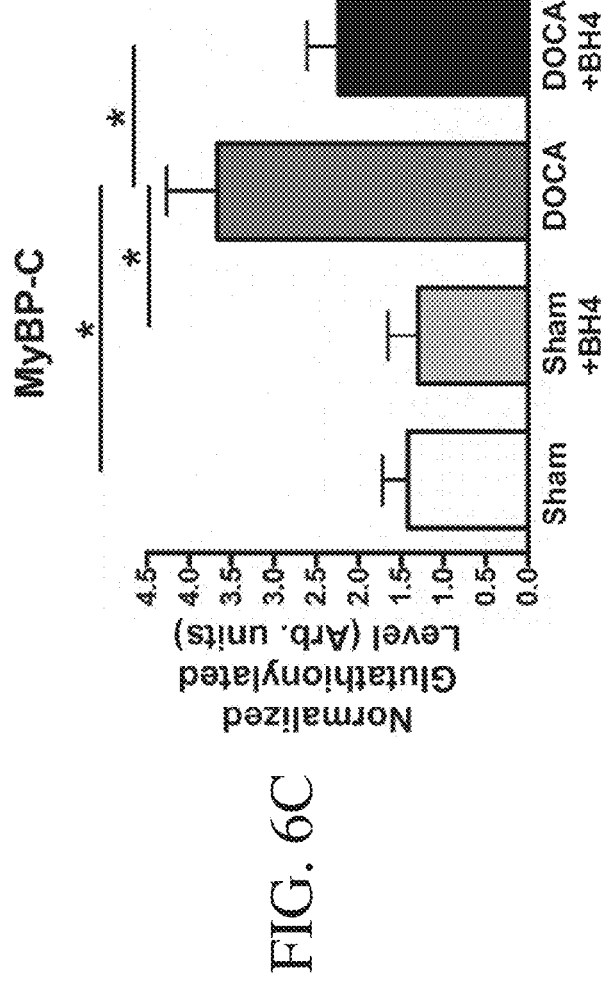
Figure 8A:
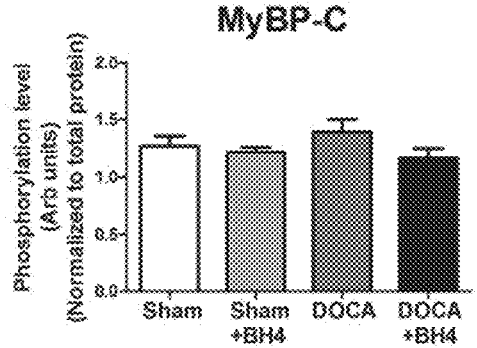
FIGS. 8A-F illustrate phosphorylation levels of myofilaments proteins normalized by total protein.
Figure 8B:
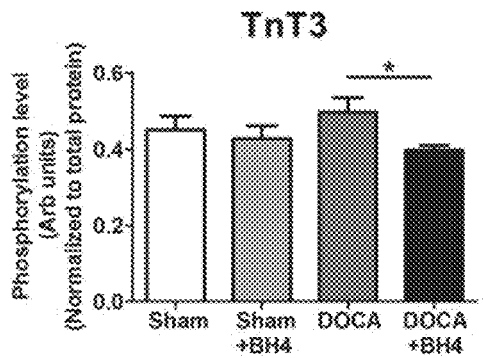
Figure 8C:
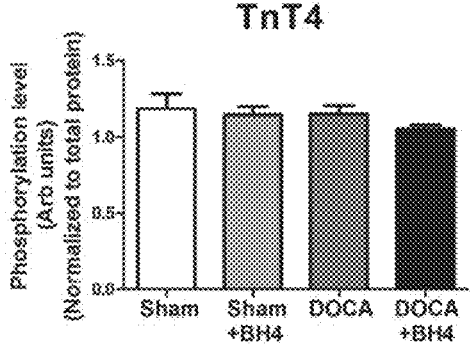
Figure 8D:
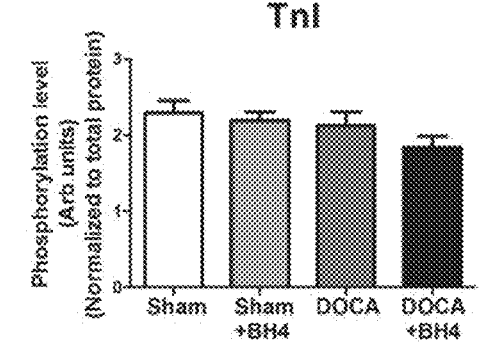
Figure 8E:
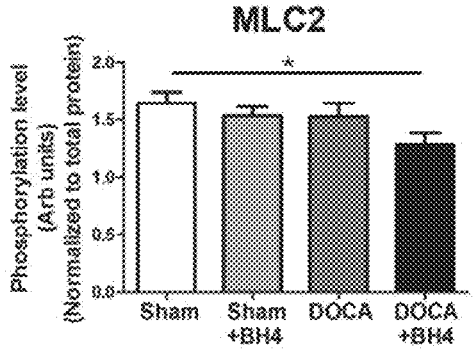
Figure 8F:
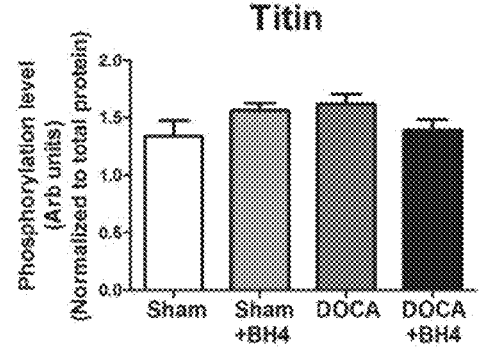
Figure 9A:
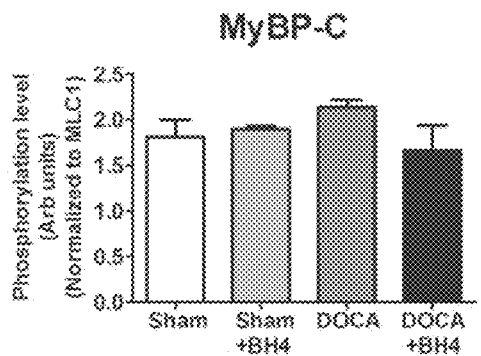
FIGS. 9A-F illustrate phosphorylation levels of myofilaments proteins normalized by MLC1.
Figure 9B:
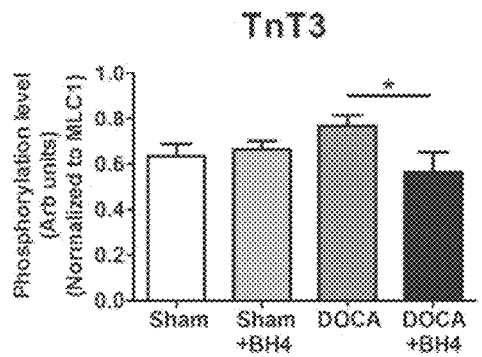
Figure 9C:
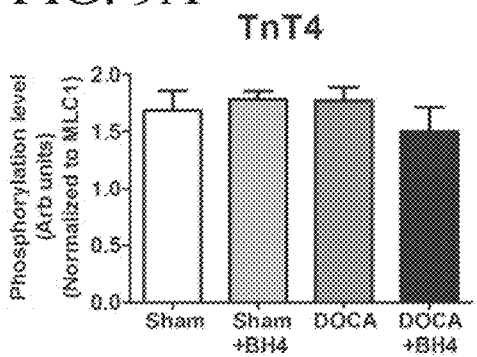
Figure 9D:
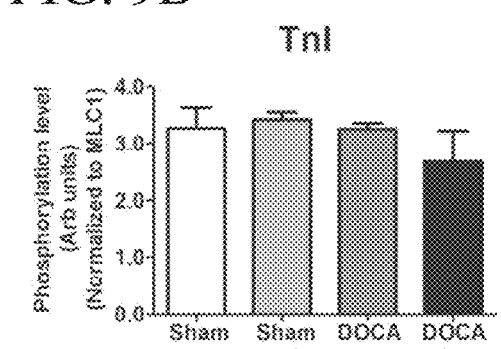
Figure 9E:
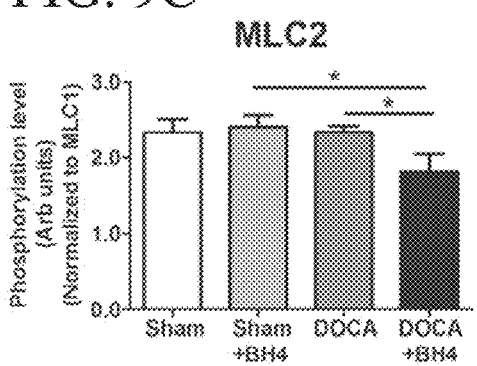
Figure 9F:
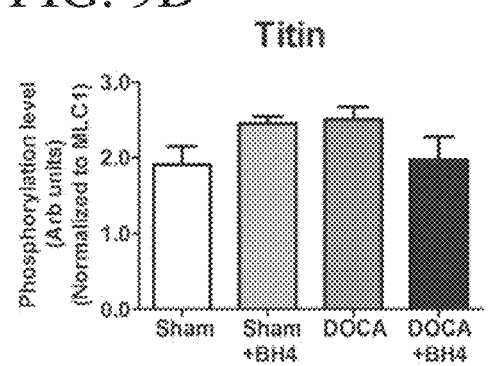
Figure 10A:
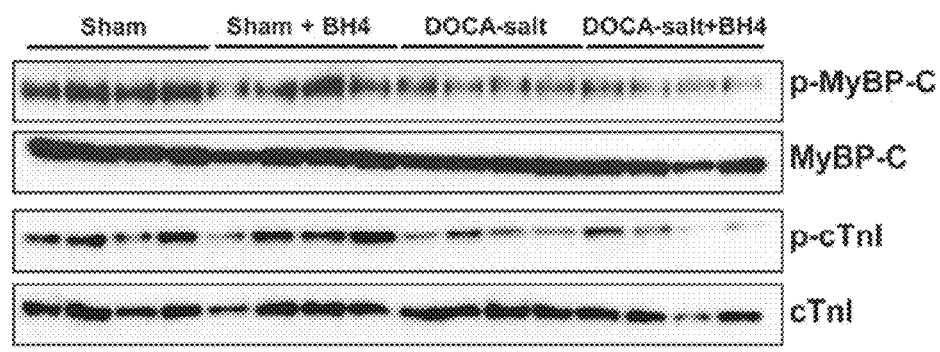
Figure 10B:
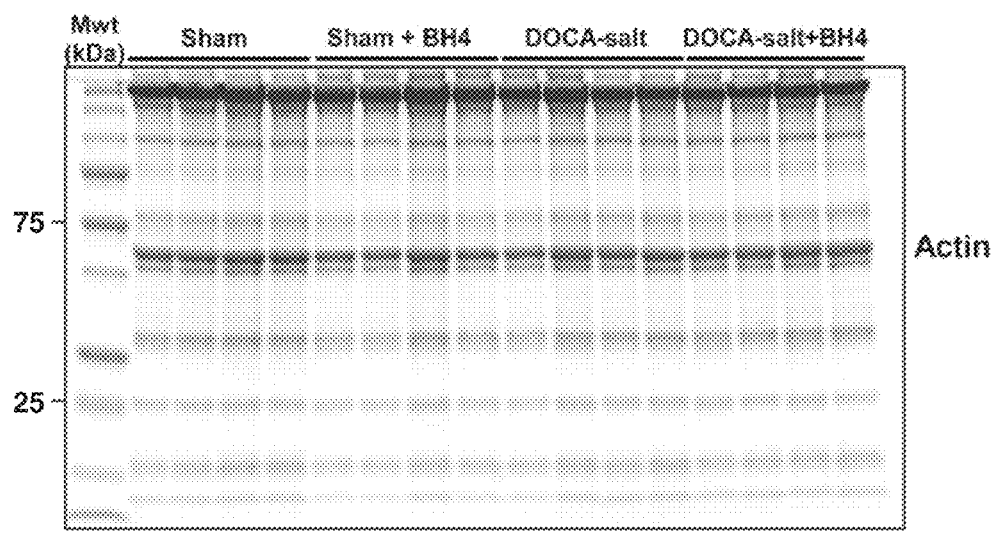
Figure 11:
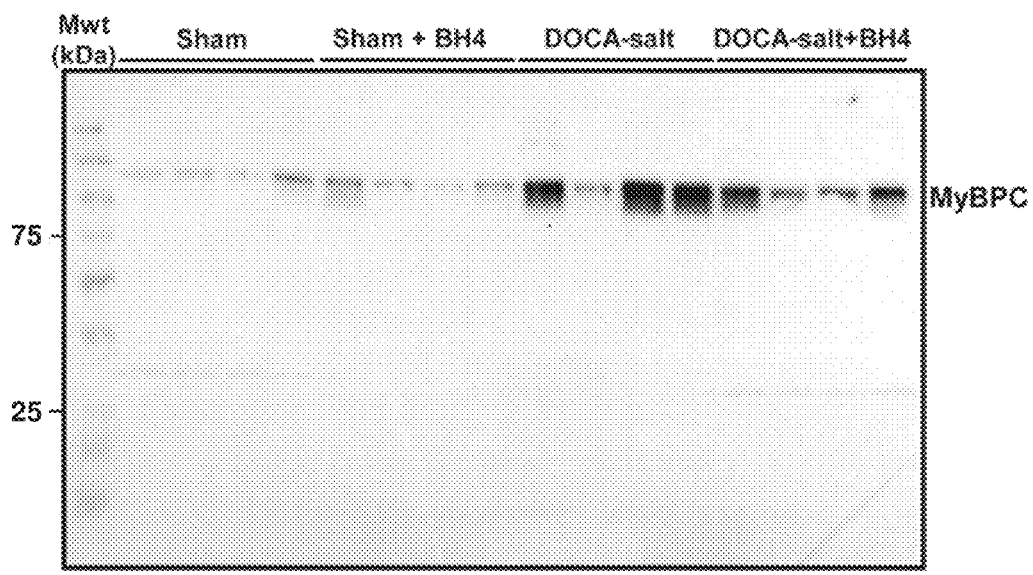
FIG. 11 illustrates glutathionylation levels of MyBP-C. Whole blot image of MyBP-C glutathionylation level against anti-glutathione antibody.

In view of my earlier findings indicating an increase in MyBP-C S-glutathionylation in cardiac myofilaments from DOCA-salt mice, I determined whether the $BH_4$ diet could reverse this modification. Representative gels and plotted data normalized to total protein loadings are shown in FIG. 6. MyBP-C glutathionylation was significantly increased in the DOCA-salt group compared to all other groups, which were not significantly different from each other. In the data shown in FIGS. 7A-H, I plotted diastolic function parameters (E/E' or E'/A' ratio) as a function of normalized MyBP-C glutathionylation. As shown in FIGS. 7A and 7B, the E/E' ratio was significantly, positively correlated with MyBP-C glutathionylation (Slope=3.23±0.90, $R^2$=0.305, P <0.01). Moreover, TDI E'/A' ratio was negatively correlated with MyBP-C glutathionylation (Slope=-0.08±0.02, $R^2$=0.257, P<0.01). Myofilament tension cost was also inversely correlated with both MyBP-C glutathionylation and E/E' echocardiographic data. However, both of phosphorylation level of TnI and MyBP-C were not significantly correlated with tension cost (FIGS. 7G-H).

Discussion

Results presented here provide new understanding of the role of cardiac myofilaments in the pharmacology and therapeutic efficacy of $BH_4$ for the treatment of diastolic dysfunction induced by pressure-overload. Overall, my results indicate that hypertension-associated diastolic dysfunction in this model likely arises mainly from a reduction in cross-bridge turnover kinetics and that administration of $BH_4$ results in amelioration of diastolic dysfunction by speeding these kinetics. Although correlative, my results support the hypothesis that changes in cross-bridge kinetics correlate with MyBP-C S-glutathionylation and that this oxidative modification may be responsible for the changes in cardiac dynamics. To the best of my knowledge, the present study is the first to report that treatment with $BH_4$ reduces increased levels of MyBP-C S-glutathionylation. Therefore, this post-translational modification may serve as a novel marker useful for the identification and treatment of diastolic heart dysfunction. Unlike in my previous study with ranolazine for the treatment of diastolic dysfunction, $BH_4$ reversed the glutathionylation of MyBP-C, suggesting that these two drugs work on the same disorder by different mechanisms (Reference 12).

Apart from my previous study indicating that S-glutathionylation correlated with changes in diastolic dysfunction and in tension cost, there is considerable evidence that modifications of MyBP-C affect diastolic function. Mutations in MyBP-C are known to induce diastolic dysfunction (Reference 25). MyBP-C is also a substrate for multiple kinases, including protein kinase (PK)A, PKC, PKD, and CaMKII (Reference 26). MyBP-C and its dephosphorylation have been shown to be associated with end stage human heart failure (Reference 27). MyBP-C dephosphorylation has also been associated with its degradation (References 26, 28-30), thick filament disruption, and contractile dysfunction (References 26, 28, 30). Phosphorylation of MyBP-C by PKA accelerates cross-bridge turnover rates (Reference 26). Interestingly, a non-PKA-phosphorylatable truncated mutant of MyBP-C (AllP-:[t/t]) exhibited a dilated LV chamber diameter, increased septal thickness, and depressed systolic function. This model also exhibited significant diastolic dysfunction because of slower cross-bridge cycling in the absence of baseline phosphorylation of MyBP-C (Reference 31). In general, my results fit with data in these studies indicating that effects of post-translational modifications in MyBP-C may be more prominently involved in altered cross-bridge kinetics and muscle dynamics than alterations in Ca-sensitivity. For example, employing loss of function models, Stelzer et al. reported that, in the intact myocardium, PKA phosphorylation of MyBP-C was a more prominent determinant of contraction and relaxation kinetics than phosphorylation of cardiac troponin 1 (cTnI), which was a more prominent determinant of Ca-sensitivity (Reference 32).

Nevertheless, in my experiments, MyBP-C phosphorylation did not correlate with diastolic dysfunction or $BH_4$ efficacy. In fact, compared to DOCA-salt myofilaments, the myofilaments from the DOCA-$BH_4$ treated hearts had reduced phosphorylation of MyBP-C as well as TnT, and MLC2. Yet $BH_4$ did not affect the phosphorylation of these proteins in the shams. A limitation of the study is that Pro-Q analysis measures total phosphorylation of a given protein, and MyBP-C contains multiple phosphorylation sites, the function of which are poorly understood. Thus, although I cannot exclude that site-specific phosphorylation may have contributed to diastolic dysfunction or the effect of $BH_4$, overall my data indicate that phosphorylation is not likely to contribute substantially to my findings of decreased tension cost and cross-bridge kinetics in the DOCA-salt myofilaments or to the amelioration of this effect with $BH_4$ treatment.

In addition to altered cross-bridge kinetics as a potential mechanism of diastolic dysfunction, modifications in sarcomeric diastolic function may be significantly affected by modifications in titin (References 33 and 34). In view of the potential modulation of extensibility by titin phosphorylation by protein kinase G (References 33 and 35), NO has been suggested to play an important role in regulating diastolic tone and ventricular filling through a cGMP-PKC dependent pathway (Reference 36). Moreover, PKG activation has been suggested to affect the reduction of $Ca^{2+}$ sensitivity through TnI phosphorylation at Ser23/24 and an increase in cross-bridge cycling rate, leading to acceleration of relaxation (References 37 and 38). However, in the present study, both titin and TnI phosphorylation were not changed by $BH_4$ treatment in DOCA-salt mice suggesting another mechanism may be involved in the relaxation improvement via $BH_4$ in this model.

An important issue is the molecular mechanism of the effect of S-glutathionylation on MyBP-C function. Possible mechanisms are couched in terms of current hypotheses as to how MyBP-C controls cross-bridge kinetics. One plausible mechanism is that the radial disposition of MyBP-C in relation to the thick filament proper is a determinant of the rates of entry of the cross-bridges into and out of the cross-bridge cycle. Proximity of cross-bridges has been demonstrated to be increased by PKA-dependent phosphorylation (Reference 39). There is also evidence that MyBP-C directly interacts with actin in the thin filaments, and it is also plausible that modulation of thin filaments may result in increased cross-bridge kinetics (Reference 40). Whatever the case, my data indicate that modification of one or more cysteine residues of MyBP-C under oxidative control by S-glutathionylation is likely to alter the proximity of the cross-bridges to or their interactions with the thin filament. In the case of the DOCA-salt model, the modification is maladaptive and induces a diastolic abnormality. It is interesting to speculate that oxidative modification of MyBP-C may also serve as an adaptive mechanism in homeostasis, which modulates cardiac relaxation reserve by controlling cross-bridge kinetics.

In summary, hypertension-induced diastolic dysfunction was characterized by reduced cross-bridge kinetics and tension cost that was reversed by $BH_4$. The effect of $BH_4$ correlated with glutathionylation of MyBP-C, suggesting that this post-translational modification may lead to diastolic dysfunction and that $BH_4$ treatment may work by preventing this oxidative modification.

EXAMPLE II

Previously, I demonstrated that the depletion of NO bioavailability caused by increased reactive oxygen species (ROS) induced diastolic dysfunction with preserved systolic function through nitric oxide synthase (NOS) uncoupling in the heart. Depletion of tetrahydrobiopterin (BH4) causes NOS uncoupling, resulting in relaxation impairment of the heart. Mitochondria are one of the major cardiac oxidative stress sources, and manganese superoxide dismutase (MnSOD) is a mitochondrial antioxidant enzyme. In the present study, I sought to determine whether heterozygous knockout of the MnSOD gene (Sod2+/−) would be associated with diastolic dysfunction (DD) that could be ameliorated by BH4.

Methods

Echocardiography was used to determine DD in heterozygous MnSOD knockout mice. The mitral annulus longitudinal velocities (E', and A') were determined by pulsed-wave tissue Doppler from the apical four-chamber view. Mitochondrial ROS were measured by confocal microscopy and flow cytometry from isolated cardiomyocytes using MitoSOX Red. NO was measured by DAF-FM and by the Griess reaction. Contraction and relaxation impairment were assessed by IonOptix System.

Results

Mitochondrial ROS were elevated by 2.6-fold and NO level was reduced by 0.77-fold in cardiomyocytes from MnSOD deficient mice. The ratio of mitral annulus longitudinal velocities (E'/A') were significantly reduced indicating DD at MnSOD deficient mice (MnSOD 0.88±0.14 vs. WT 1.11±0.11). Resting sarcomere length was significantly reduced in MnSOD deficient cardiomyocytes compared to WT (MnSOD 1.68±0.01 μm vs. WT 1.84±0.01 μm, P<0.001) and the relaxation constant (tau) was significantly increased (MnSOD 0.12±0.01 vs. WT 0.09±0.01, P<0.05). BH4 treatment improved resting sarcomere length (1.77±0.01 μm, P<0.001) and tau (0.73±0.01, P<0.001) compared to MnSOD.

Conclusions

MnSOD deficiency was associated with impaired cardiac relaxation indicating DD, which could be improved with BH4 treatment.

TABLE 1

Transthoracic Echocardiography Measurements
In Vivo BH$_4$ Treatment in DOCA-Salt Mice

| | Sham | Sham + BH$_4$ | DOCA-salt | DOCA-salt + BH$_4$ |
|---|---|---|---|---|
| LV M-Mode Protocol | | | | |
| EF (%) | 56.3 ± 3.9 | 51.1 ± 2.8 | 51.9 ± 4.4 | 54.5 ± 5.0 |
| FS (%) | 28.9 ± 2.8 | 24.7 ± 1.6 | 26.4 ± 2.7 | 26.6 ± 2.9 |
| LVESD (mm) | 2.74 ± 0.16 | 3.01 ± 0.11 | 2.86 ± 0.18 | 2.65 ± 0.21 |
| LVEDD (mm) | 3.86 ± 0.08 | 4.05 ± 0.10† | 3.87 ± 0.11 | 3.67 ± 0.14† |
| Mitral Valve Protocol | | | | |
| MV E (mm/s) | 698.2 ± 35.9^ | 738.1 ± 31.1†& | 613.7 ± 45.8& | 555.0 ± 35.1†^ |
| MV A (mm/s) | 326.8 ± 30.1 | 357.5 ± 31.7 | 329.2 ± 48.7 | 367.8 ± 48.3 |
| MV E/A ratio | 2.31 ± 0.31 | 2.28 ± 0.33 | 2.15 ± 0.46 | 1.71 ± 0.33 |
| Tissue Doppler Protocol | | | | |
| E' (mm/s) | 22.3 ± 1.7^* | 24.4 ± 2.2†& | 14.3 ± 0.8&* | 16.8 ± 1.3†^ |
| A' (mm/s) | 19.4 ± 1.9 | 21.1 ± 1.9† | 20.1 ± 1.4‡ | 15.2 ± 1.0†‡ |
| E'/A' ratio | 1.20 ± 0.09* | 1.17 ± 0.06& | 0.74 ± 0.05‡*& | 1.12 ± 0.10‡ |
| E/E' ratio | 30.38 ± 1.17* | 34.91 ± 6.81& | 43.69 ± 2.73*&‡ | 34.53 ± 2.22‡ |
| Sm | 20.8 ± 1.8 | 22.9 ± 1.5† | 18.5 ± 1.6 | 15.8 ± 1.5† |

EF, ejection fraction;
FS, fractional shortening;
LVESD, left ventricle end systolic diameter;
LVEDD, left ventricle end diastolic diameter;
MV, mitral valve;
MV E, mitral inflow velocity peak early filing;
MV A, mitral inflow velocity peak late filing;
E', mitral annulus longitudinal velocity tissue Doppler early filing rate;
A' mitral annulus longitudinal velocity tissue Doppler late filing rate;
Sm, mitral annulus longitudinal velocity tissue Doppler systolic velocity. Data are represented as mean ± SEM (n = 7-9 per group).
$P < 0.05$ for Sham vs. Sham + BH$_4$.
*$P < 0.05$ for Sham vs. DOCA-salt.
†$P < 0.05$ for Sham + BH$_4$ vs. DOCA-salt + BH$_4$.
‡$P < 0.05$ for DOCA-salt vs. DOCA-salt + BH$_4$.
^$P < 0.05$ for Sham vs. DOCA-salt + BH$_4$.
&$P < 0.05$ for Sham + BH$_4$ vs. DOCA-salt.

TABLE 2

Isolated Myocyte Contraction And Relaxation Parameters

| | Sham | Sham + BH$_4$ | DOCA-salt | DOCA-salt + BH$_4$ |
|---|---|---|---|---|
| Diastolic SL, μm | 1.78 ± 0.01*# | 1.80 ± 0.01#† | 1.70 ± 0.01*&‡ | 1.77 ± 0.01†‡ |
| Systolic SL, μm | 1.59 ± 0.01* | 1.61 ± 0.01& | 1.54 ± 0.01*&‡ | 1.60 ± 0.01‡ |
| Sarcomere shortening, % | 9.47 ± 0.41 | 10.64 ± 0.61& | 9.14 ± 0.44& | 9.48 ± 0.49 |
| Shortening velocity, μm/s | −2.38 ± 0.11# | −2.90 ± 0.16#†& | −2.03 ± 0.12&‡ | −2.42 ± 0.14†‡ |
| Time to peak shortening, ms | 147.1 ± 5.2* | 133.6 ± 0.3& | 185.7 ± 6.8*&‡ | 146.2 ± 0.3‡ |
| Time to 50% shortening, ms | 47.3 ± 1.0* | 45.6 ± 0.8 | 50.9 ± 1.3*‡ | 47.5 ± 0.7‡ |
| Time to 90% shortening, ms | 96.6 ± 2.4*# | 87.3 ± 1.8&# | 111.2 ± 3.6*&‡ | 93.5 ± 1.8‡ |
| Relengthening velocity, μm/s | 2.09 ± 0.11*# | 2.75 ± 0.18#†& | 1.60 ± 0.15*&‡ | 2.39 ± 0.18†‡ |
| Time to 50% relengthening, ms | 271.8 ± 10.9*# | 204.7 ± 6.0&# | 348.7 ± 15.4*&‡ | 240.3 ± 7.5‡ |
| Time to 90% relengthening, ms | 258.4 ± 26.0*# | 258.7 ± 11.7&# | 444.5 ± 19.6*&‡ | 300.0 ± 13.4‡ |
| Relaxation constant, τ | 0.09 ± 0.01* | 0.07 ± 0.00& | 0.28 ± 0.02*&‡ | 0.08 ± 0.01‡ |
| No. of mice/cells | 6/79 | 4/43 | 5/85 | 4/57 |

SL, sarcomere length. Measurements were performed under 1.0-Hz electrical stimulation, 10 V, in the presence of external Ca$^{2+}$ of 1.2 mmol/L. Data are mean ± SEM.
N = 43-85 cardiomyocytes from 4-6 mice per group.
$P < 0.05$ for Sham vs. Sham + BH$_4$.
*$P < 0.05$ for Sham vs. DOCA-salt.
†$P < 0.05$ for Sham + BH$_4$ vs. DOCA-salt + BH$_4$.
‡$P < 0.05$ for DOCA-salt vs. DOCA-salt + BH$_4$.
^$P < 0.05$ for Sham vs. DOCA-salt + BH$_4$.
&$P < 0.05$ for Sham + BH$_4$ vs. DOCA-salt.

TABLE 3

Effect Of $BH_4$ On Tension And ATPase Rate of Skinned Fiber Bundles

| | Sham | Sham + $BH_4$ | DOCA-salt | DOCA-salt + $BH_4$ |
|---|---|---|---|---|
| Maximum ATPase (pmol * s−1 * mg−1) | 197.8 ± 2.3#*^ | 256.0 ± 1.7#† | 177.5 ± 2.0*‡ | 296.0 ± 4.7†‡^ |
| pCa50 for Tension | 5.739 ± 0.006*^ | 5.753 ± 0.004 | 5.776 ± 0.004* | 5.766 ± 0.005^ |
| Maximum Tension (mN/mm²) | 22.22 ± 0.19#*^ | 30.43 ± 0.19#† | 24.92 ± 0.15*‡ | 33.04 ± 0.25†‡^ |
| Tension Cost ΔATPase/ΔTension | 8.5 ± 0.3* | 7.9 ± 0.3 | 6.5 ± 0.2*‡ | 7.4 ± 0.4‡ |

Data are means ± SEM.
N = 9-17 fibers,
p < 0.05 for Sham vs. Sham + $BH_4$.
*P < 0.05 for Sham vs. DOCA-salt.
†p < 0.05 for Sham + $BH_4$ vs. DOCA-salt + $BH_4$.
‡P < 0.05 for DOCA-salt vs. DOCA-salt + $BH_4$.
^P < 0.05 for Sham vs. DOCA-salt + $BH_4$.

While this invention has been described as having preferred sequences, ranges, steps, order of steps, materials, structures, shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

REFERENCES

The following references, and those cited in the disclosure herein, are hereby incorporated herein in their entirety by reference.

[1] Schocken D D, Benjamin E J, Fonarow G C, Krumholz H M, Levy D, Mensah G A et al. Prevention of heart failure: a scientific statement from the American Heart Association Councils on Epidemiology and Prevention, Clinical Cardiology, Cardiovascular Nursing, and High Blood Pressure Research; Quality of Care and Outcomes Research Interdisciplinary Working Group; and Functional Genomics and Translational Biology Interdisciplinary Working Group. Circulation 2008; 117:2544-65.
[2] Owan T E, Hodge D O, Herges R M, Jacobsen S J, Roger V L, Redfield M M. Trends in prevalence and outcome of heart failure with preserved ejection fraction. N Engl J Med 2006; 355:251-9.
[3] Ouzounian M, Lee D S, Liu P P. Diastolic heart failure: mechanisms and controversies. Nat Clin Pract Cardiovasc Med 2008; 5:375-86.
[4] Ziolo M T, Kohr M J, Wang H. Nitric oxide signaling and the regulation of myocardial function. J Mol Cell Cardiol 2008; 45:625-32.
[5] Landmesser U, Dikalov S, Price S R, McCann L, Fukai T, Holland S M et al. Oxidation of tetrahydrobiopterin leads to uncoupling of endothelial cell nitric oxide synthase in hypertension. J Clin Invest 2003; 111:1201-9.
[6] Flesch M, Kilter H, Cremers B, Lenz O, Sudkamp M, Kuhn-Regnier F et al. Acute effects of nitric oxide and cyclic GMP on human myocardial contractility. J Pharmacol Exp Ther 1997; 281:1340-9.
[7] Prabhu S D, Azimi A, Frosto T. Nitric oxide effects on myocardial function and force-interval relations: regulation of twitch duration. J Mol Cell Cardiol 1999; 31:2077-85.
[8] Ruetten H, Dimmeler S, Gehring D, Ihling C, Zeiher A M. Concentric left ventricular remodeling in endothelial nitric oxide synthase knockout mice by chronic pressure overload. Cardiovasc Res 2005; 66:444-53.
[9] Ungureanu-Longrois D, Bezie Y, Perret C, Laurent S. Effects of exogenous and endogenous nitric oxide on the contractile function of cultured chick embryo ventricular myocytes. J Mol Cell Cardiol 1997; 29:677-87.
[10] Silberman G A, Fan T H, Liu H, Jiao Z, Xiao H D, Lovelock J D et al. Uncoupled cardiac nitric oxide synthase mediates diastolic dysfunction. Circulation 2010; 121:519-28.
[11] Vasquez-Vivar J, Kalyanaraman B. Generation of superoxide from nitric oxide synthase. FEBS Lett 2000; 481:305-6.
[12] Lovelock J D, Monasky M M, Jeong E M, Lardin H A, Liu H, Patel B G et al. Ranolazine improves cardiac diastolic dysfunction through modulation of myofilament calcium sensitivity. Circ Res 2012; 110:841-50.
[13] Adachi T, Weisbrod R M, Pimentel D R, Ying J, Sharov V S, Schoneich C et al. S-Glutathiolation by peroxynitrite activates SERCA during arterial relaxation by nitric oxide. Nat Med 2004; 10:1200-7.
[14] Adachi T, Pimentel D R, Heibeck T, Hou X, Lee Y J, Jiang B et al. S-glutathiolation of Ras mediates redox-sensitive signaling by angiotensin II in vascular smooth muscle cells. J Biol Chem 2004; 279:29857-62.
[15] Chen F C, Ogut O. Decline of contractility during ischemia-reperfusion injury: actin glutathionylation and its effect on allosteric interaction with tropomyosin. Am J Physiol Cell Physiol 2006; 290:C719-C727.
[16] Kagawa K, Horiuti K, Yamada K. BDM compared with P, and low $Ca^{2+}$ in the cross-bridge reaction initiated by flash photolysis of caged ATP. Biophys J 1995; 69:2590-600.
[17] Wolska B M, Keller R S, Evans C C, Palmiter K A, Phillips R M, Muthuchamy M et al. Correlation between myofilament response to $Ca^{2+}$ and altered dynamics of contraction and relaxation in transgenic cardiac cells that express beta-tropomyosin. Circ Res 1999; 84:745-51.
[18] de Tombe P P, Stienen G J. Protein kinase A does not alter economy of force maintenance in skinned rat cardiac trabeculae. Circ Res 1995; 76:734-41.
[19] de Tombe P P, ter Keurs H E. Force and velocity of sarcomere shortening in trabeculae from rat heart. Effects of temperature. Circ Res 1990; 66:1239-54.

[20] Martin A F, Phillips R M, Kumar A, Crawford K, Abbas Z, Lessard J L et al. $Ca^{2+}$ activation and tension cost in myofilaments from mouse hearts ectopically expressing enteric gamma-actin. Am J Physiol Heart Circ Physiol 2002; 283:H642-H649.

[21] Layland J, Cave A C, Warren C, Grieve D J, Sparks E, Kentish J C et al. Protection against endotoxemia-induced contractile dysfunction in mice with cardiac-specific expression of slow skeletal troponin I. FASEB J 2005; 19:1137-9.

[22] Hill B G, Ramana K V, Cai J, Bhatnagar A, Srivastava S K. Measurement and identification of S-glutathiolated proteins. Methods Enzymol 2010; 473:179-97.

[23] Biesiadecki B J, Kobayashi T, Walker J S, John S R, de Tombe P P. The troponin C G159D mutation blunts myofilament desensitization induced by troponin I Ser23/24 phosphorylation. Circ Res 2007; 100:1486-93.

[24] Tong C W, Stelzer J E, greater M L, Powers P A, Moss R L. Acceleration of crossbridge kinetics by protein kinase A phosphorylation of cardiac myosin binding protein C modulates cardiac function. Circ Res 2008; 103:974-82.

[25] Fraysse B, Weinberger F, Bardswell S C, Cuello F, Vignier N, Geertz B et al. Increased myofilament $Ca^{2+}$ sensitivity and diastolic dysfunction as early consequences of Mybpc3 mutation in heterozygous knock-in mice. J Mol Cell Cardiol 2012; 52:1299-307.

[26] Barefield D, Sadayappan S. Phosphorylation and function of cardiac myosin binding protein-C in health and disease. J Mol Cell Cardiol 2010; 48:866-75.

[27] El-Armouche A, Pohlmann L, Schlossarek S, Starbatty J, Yeh Y H, Nattel S et al. Decreased phosphorylation levels of cardiac myosin-binding protein-C in human and experimental heart failure. J Mol Cell Cardiol 2007; 43:223-9.

[28] Decker R S, Decker M L, Kulikovskaya I, Nakamura S, Lee D C, Harris K et al. Myosin-binding protein C phosphorylation, myofibril structure, and contractile function during low-flow ischemia. Circulation 2005; 111:906-12.

[29] Yuan C, Guo Y, Ravi R, Przyklenk K, Shilkofski N, Diez R et al. Myosin binding protein C is differentially phosphorylated upon myocardial stunning in canine and rat hearts—evidence for novel phosphorylation sites. Proteomics 2006; 6:4176-86.

[30] Sadayappan S, Osinska H, Klevitsky R, Lorenz J N, Sargent M, Molkentin J D et al. Cardiac myosin binding protein C phosphorylation is cardioprotective. Proc Natl Acad Sci USA 2006; 103:16918-23.

[31] Sadayappan S, Gulick J, Osinska H, Martin L A, Hahn H S, Dorn G W et al. Cardiac myosin-binding protein-C phosphorylation and cardiac function. Circ Res 2005; 97:1156-63.

[32] Stelzer J E, Patel J R, Walker J W, Moss R L. Differential roles of cardiac myosin-binding protein C and cardiac troponin I in the myofibrillar force responses to protein kinase A phosphorylation. Circ Res 2007; 101:503-11.

[33] Fukuda N, Wu Y, Nair P, Granzier H L. Phosphorylation of titin modulates passive stiffness of cardiac muscle in a titin isoform-dependent manner. J Gen Physiol 2005; 125:257-71.

[34] Yamasaki R, Wu Y, McNabb M, greater M, Labeit S, Granzier H. Protein kinase A phosphorylates titin's cardiac-specific N2B domain and reduces passive tension in rat cardiac myocytes. Circ Res 2002; 90:1181-8.

[35] Kruger M, Kotter S, Grutzner A, Lang P, Andresen C, Redfield M M et al. Protein kinase G modulates human myocardial passive stiffness by phosphorylation of the titin springs. Circ Res 2009; 104:87-94.

[36] Shah A M, Prendergast B D, Grocott-Mason R, Lewis M J, Paulus W J. The influence of endothelium-derived nitric oxide on myocardial contractile function. Int J Cardiol 1995; 50:225-31.

[37] Layland J, Li J M, Shah A M. Role of cyclic GMP-dependent protein kinase in the contractile response to exogenous nitric oxide in rat cardiac myocytes. J Physiol 2002; 540:457-67.

[38] Shah A M, Spurgeon H A, Sollott S J, Talo A, Lakatta E G. 8-bromo-cGMP reduces the myofilament response to Ca2+ in intact cardiac myocytes. Circ Res 1994; 74:970-8.

[39] Colson B A, Locher M R, Bekyarova T, Patel J R, Fitzsimons D P, Irving T C et al. Differential roles of regulatory light chain and myosin binding protein-C phosphorylations in the modulation of cardiac force development. J Physiol 2010; 588:981-93.

[40] Harris S P, Lyons R G, Bezold K L. In the thick of it: HCM-causing mutations in myosin binding proteins of the thick filament. Circ Res 2011; 108:751-64.

[41] Yates L D, greater M L. Quantitative determination of myosin and actin in rabbit skeletal muscle. J Mol Biol 1983; 168:123-41.

[42] Fritz J D, Swartz D R, greater M L. Factors affecting polyacrylamide gel electrophoresis and electroblotting of high-molecular-weight myofibrillar proteins. Anal Biochem 1989; 180:205-10.

[43] Vahebi S, Kobayashi T, Warren C M, de Tombe P P, Solaro R J. Functional effects of rho-kinase-dependent phosphorylation of specific sites on cardiac troponin. Circ Res 2005; 96:740-7.

[44] Borgstahl, Cell 71; 107, 1992.

[45] McCord & Fridovch, JBC 244:6049, 1969.

[46] Liochev and Fridovich, 2007.

[47] Dikalove et al. Circ Res. 2010 Jul. 9; 107(1):106-16.

What is claimed is:

1. A method of treating, reversing, or ameliorating diastolic dysfunction in a host with normal systolic function, comprising:
    a) providing a host with normal systolic function with an ejection fraction of 50% or greater, and in need of treating, reversing, or ameliorating diastolic dysfunction; and
    b) reducing S-glutathionylated myosin binding protein-C (MyBP-C) level by administering to the host a therapeutically effective amount of tetrahydrobiopterin ($BH_4$).

2. The method of claim 1, wherein the step of administering comprises:
    administering $BH_4$ in at least one form selected from the group consisting of a dietary supplement, a composition, a pharmaceutical composition, and a combination thereof.

3. The method of claim 1, wherein the step of administering comprises:
    administering $BH_4$ orally.

4. The method of claim 1, wherein the host is a human.

5. The method of claim 1, wherein the host is an animal.

6. A method of treating, preventing, reversing, or ameliorating diastolic dysfunction, comprising: modulating post-translational modification of myosin binding protein-C (MyBP-C) level by administering to a host in need thereof a therapeutically effective amount of tetrahydrobiopterin (BH4).

7. The method of claim 6, wherein the step of administering comprises: administering BH4 in at least one form selected from the group consisting of a dietary supplement, a composition, a pharmaceutical composition, and a combination thereof.

8. The method of claim 6, wherein the step of administering comprises: administering BH4 orally.

9. The method of claim 6, wherein the host is a human.

10. The method of claim 6, wherein the host is an animal.

* * * * *